(12) United States Patent
Nakamura et al.

(10) Patent No.: US 8,138,167 B2
(45) Date of Patent: Mar. 20, 2012

(54) METHODS FOR TREATING LUNG CANCERS

(75) Inventors: Yusuke Nakamura, Bunkyo-ku (JP); Yataro Daigo, Bunkyo-ku (JP)

(73) Assignee: Oncotherapy Science, Inc., Kanagawa (JP)

( * ) Notice: Subject to any disclaimer, the term of this patent is extended or adjusted under 35 U.S.C. 154(b) by 699 days.

(21) Appl. No.: 12/278,763

(22) PCT Filed: Feb. 10, 2006

(86) PCT No.: PCT/JP2006/302345
§ 371 (c)(1),
(2), (4) Date: Dec. 10, 2008

(87) PCT Pub. No.: WO2007/091328
PCT Pub. Date: Aug. 16, 2007

(65) Prior Publication Data
US 2009/0186892 A1    Jul. 23, 2009

(51) Int. Cl.
*A01N 43/00*    (2006.01)

(52) U.S. Cl. .................. 514/183; 514/234.1; 514/265.1; 436/6

(58) Field of Classification Search ................. 514/183, 514/234.5, 265.1; 436/6
See application file for complete search history.

(56) References Cited

U.S. PATENT DOCUMENTS

| | | | |
|---|---|---|---|
| 2003/0086924 A1* | 5/2003 | Sliwkowski | 424/143.1 |
| 2005/0260639 A1 | 11/2005 | Nakamura et al. | |
| 2006/0024692 A1 | 2/2006 | Nakamura et al. | |
| 2007/0269432 A1 | 11/2007 | Nakamura et al. | |
| 2009/0286856 A1 | 11/2009 | Nakamura et al. | |

FOREIGN PATENT DOCUMENTS

| | | |
|---|---|---|
| WO | WO 2004/031412 A2 | 4/2004 |
| WO | WO 2004/031413 A2 | 4/2004 |
| WO | WO 2005/028676 A2 | 3/2005 |
| WO | WO 2005/149829 A2 | 6/2005 |

OTHER PUBLICATIONS

"Gefitinib" Saikin no Shin'yaku 2003, Kabushiki Kaisha Yakuji Nipposha, May 9, 2003, pp. 73-80.
Ishikawa, et al., "Prediction of response of advanced non-small cell lung cancers to gefitinib using serum markers," Sep. 14, 2005, *Biotechnology Japan*. Abstract only. http://biotech.nikkeibp.cojp/bionewsn/detail.jsp?id=20032032.
Ishikawa, et al., "Prediction of response of advanced non-small cell lung cancers to gefitinib using serum markers [abstract]." In: Sixty-Fourth Annual Meeting of the Japanese Cancer Association; Sep. 14-16, 2005; Sapporo, JP; JCA: 2005; p. 41, Abstract #W-030.
Ishikawa, et al., "Increases of Amphiregulin and Transforming Growth Factor-α in Serum as Predictors of Poor Response to Gefitinib among Patients with Advanced Non-Small Lung Cancers," 2005, *Cancer Research*, vol. 65, No. 20, pp. 9176-9184.
Kakuichi, et al., "Prediction of sensitivity of advanced non-small cell lung cancers to gefitinib (Iressa, ZD1839)," 2004, *Human Molecular Genetics*, vol. 13, No. 24, pp. 3029-3043.
"Gefitinib" Saikin no Shin'yaku 2003, Kabushiki Kaisha Yakuji Nipposha, May 9, 2003, pp. 73-80, (2003).
Ishikawa, et al., "Prediction of response of advanced non-small cell lung cancers to gefitinib using serum markers," Sep. 14, 2005, *Biotechnology Japan*. Abstract only. http://biotech.nikkeibp.cojp/bionewsn/detail.jsp?id=20032032, (2005).
Ishikawa, et al., "Prediction of response of advanced non-small cell lung cancers to gefitinib using serum markers [abstract]." In: Sixty-Fourth Annual Meeting of the Japanese Cancer Association; Sep. 14-16, 2005; Sapporo, JP; JCA: 2005; p. 41, Abstract #W-030, (2005).
Ishikawa, et al., "Increases of Amphiregulin and Transforming Growth Factor-α in Serum as Predictors of Poor Response to Gefitinib among Patients with Advanced Non-Small Lung Cancers," 2005, *Cancer Research*, vol. 65, No. 20, pp. 9176-9184, (2005).
Kakuichi, et al., "Prediction of sensitivity of advanced non-small cell lung cancers to gefitinib (Iressa, ZD1839)," 2004, *Human Molecular Genetics*, vol. 13, No. 24, pp. 3029-3043, (2004).
U.S. Appl. No. 13/238,273, filed Sep. 21, 2011, 118 pgs, (2011).

* cited by examiner

*Primary Examiner* — Jeffrey S. Lundgren
*Assistant Examiner* — Ibrahim D Bori
(74) *Attorney, Agent, or Firm* — Kilpatrick Townsend & Stockton LLP

(57) ABSTRACT

The present invention provided methods for treating lung cancers using therapeutic agents for lung cancers comprising erbB receptor inhibitors as active ingredients. Methods for examining the responsiveness of lung cancer patients to erbB receptor inhibitors by using blood amphiregulin (AREG) as an indicator were provided. Furthermore, methods for treating lung cancers in which responsiveness to an erbB receptor inhibitor is determined based on blood AREG concentration, and in which therapeutic agents are selectively administered to patients expected to be responsive, were also provided. Advanced therapeutic effects can be expected by administering an erbB receptor inhibitor to patients predicted to be responsive. The present invention contributes to the improvement of therapeutic effects of gefitinib (Product name: Iressa®) and such on lung cancers.

4 Claims, 3 Drawing Sheets

A

B

A

B

METHODS FOR TREATING LUNG CANCERS

CROSS REFERENCE TO RELATED APPLICATIONS

This application is a U.S. National Phase of PCT/JP2006/302345, filed Feb. 10, 2006, the contents of which is herein incorporated by reference.

TECHNICAL FIELD

The present invention relates to lung cancer treatments.

BACKGROUND ART

Epidermal growth factor receptor (EGFR) plays an important role in the growth of solid cancers derived from a variety of tissues, and is overexpressed in 40% to 80% of non-small-cell lung cancers examined (Salomon D S, et al., Crit. Rev. Oncol. Hematol. 1995; 19:183-232; and Mendelsohn J, et al., Oncogene 2000; 19:6550-65). Overexpression of EGFR is also associated with a poor prognosis for lung cancer patients (Selvaggi G, et al., Ann. Oncol. 2004; 15:28-32). Gefitinib (Iressa, ZD1839) is an orally administered inhibitor of EGFR tyrosine kinase, a key enzyme in the EGFR signaling pathway, which is involved in the diffusion, invasion, and survival of cancer cells (Wakeling A E, et al., Cancer Res 2002; 62:5749-54).

Gefitinib has demonstrated effective antitumor effects in clinical trials enrolling patients with progressive non-small-cell lung cancers, for whom chemotherapy using platinum formulations had not demonstrated favorable effects (Fukuoka M, et al., J. Clin. Oncol. 2003; 21:2237-46.; Kim Y H, et al., Clin. Cancer Res. 2004; 10:7311-7). Based on these findings, gefitinib has been used for the treatment of advanced non-small-cell lung cancers in several countries including Japan, Australia, and the United States.

Approximately 37,000 patients with advanced non-small-cell lung cancer have been treated with this drug in Japan since its approval (Evans T L. Oncologist 2004; 9:232-8). Although gefitinib has been effective in improving the prognosis and QOL of many of those Japanese patients, 60% of them have shown no improvement in symptoms. Not only that, but 5.4% of the patients have developed severe gefitinib-induced acute interstitial lung disease (Takano T, et al., Lung Cancer 2004; 45:93-104). Therefore, an indicator that enables physicians to select patients for whom gefitinib will be efficacious is required.

However, none of the factors examined so far, including somatic EGFR mutations, have been able to determine patient responsiveness to gefitinib administration from the viewpoint of disease control or benefit to survival. Specifically, there are currently no known indicators that enable an accurate distinction between patients with low gefitinib responsiveness and patients who are responsive to gefitinib.

There are reports that patients likely to show a partial response (PR) to gefitinib can be predicted based on the presence of EGFR mutations. However, it is not possible to show clearly that patients maintaining a stable condition could gain some survival advantage (Lynch T J, et al., N. Engl. J. Med. 2004; 350:2129-39.; Paez J G et al., Science 2004; 304:1497-500.; Pao W, et al., Proc. Natl. Acad. Sci. USA 2004; 101:13306-11.; Tokumo M, et al., Clin. Cancer Res. 2005; 11:1167-73.; Mitsudomi T, et al., J. Clin. Oncol. 2005; 23:2513-20).

Recently, twelve genes associated with sensitivity to gefitinib were identified through statistical analysis of expression information on genes that are expressed in advanced non-small-cell lung cancers. In addition, a gefitinib response scoring system has been proposed based on the expression level of genes whose expression levels vary greatly between a group of patients who partially respond to gefitinib administration (PR), and a group for whom the disease progresses (PD) (Kakiuchi S, et al., Hum. Mol. Genet. 2004; 13:3029-43.; WO 2005/49829).

Patent Document 1: WO 2005/49829
Non-Patent Document 1: Kakiuchi S, et al., Hum. Mol. Genet. 2004; 13:3029-43.

DISCLOSURE OF THE INVENTION

Problems to be Solved by the Invention

An objective of the present invention is to provide novel techniques for treating lung cancers. Specifically, it provides techniques for distinguishing between lung cancer patients who are responsive to erbB receptor inhibitors, typified by gefitinib, and patients who show low responsiveness, which enables administration of erbB receptor inhibitors to patients who are expected to be responsive. Alternatively, a preferred embodiment of the present invention provides techniques that enable highly sensitive detection of patients with low responsiveness to erbB receptor inhibitors.

Means to Solve the Problems

The results of predictions based on the gefitinib response scoring system (Kakiuchi S, et al., Hum. Mol. Genet. 2004; 13:3029-43.; WO 2005/49829) were in accordance with the clinical responses to gefitinib for all additional test cases (PR and PD). Moreover, this system was able to separate the group of patients for whom the disease condition was stable (SD) into two groups: a group of patients who can maintain the tumor in a stable condition for a long period, and a group of patients who can not. However, analysis of expression profiles or mutations requires the acquisition of clinical samples by biopsy or surgery. In reality, biopsy or surgery is not ordinarily carried out in cases of advanced non-small cell lung cancer. Therefore, obtaining the samples necessary for scoring from patients is difficult. Thus, the gefitinib response scoring system is a difficult method to apply in clinics.

Therefore, development of practical diagnostic methods that can predict the sensitivity or resistance of lung cancer to gefitinib therapy by using serological markers is urgently desired. As a step towards that goal, the cDNA microarray analysis mentioned above revealed that genes encoding two EGFR ligands—amphiregulin (hereinafter also referred to as AREG) and transforming growth factor-alpha (TGF-α, hereinafter also referred to as TGFA)—were overexpressed in tumor tissues obtained from patients who were not responsive to gefitinib (Kakiuchi S, et al., Hum Mol Genet 2004; 13:3029-43). The possibility of using the serum TGFA level as an indicator for predicting responsiveness to gefitinib has also been indicated (WO 2005/49829).

Nonetheless, when blood TGFA level alone is used as an indicator, more than half of the non-responsive patients cannot be differentiated from responsive patients. Specifically, almost all (approximately 95%) of the patients considered positive based on blood TGFA levels were patients with a low response to gefitinib. On the other hand, those patients considered negative based on blood TGFA levels included many patients whose response to gefitinib was low. That is, blood TGFA level is an indicator that shows high specificity, but leaves room for improvement in terms of sensitivity when detecting patients whose responsiveness to gefitinib is low.

Therefore, methods that can accurately distinguish between gefitinib-responsive patients and non-responsive patients are in demand. More specifically, an objective of the present invention is to improve the sensitivity of detection of patients with low responsiveness to gefitinib.

The prediction of gefitinib responsiveness by using a substance in blood as an indicator has the following advantages:

easy collection of test samples (blood): for example, compared to biopsy samples or the removal of cancer tissues by surgical operation, the collection of blood samples is clearly less of a burden (less invasive) for patients; and easy to make quantitative measurements: the advantages of blood markers include being able to rapidly and quantitatively analyze them using simple methods such as immunological measurement methods.

However, blood TGFA, a known marker for predicting responsiveness to gefitinib, still has room for improvement in terms of sensitivity in detecting patients whose responsiveness to gefitinib is low. Sensitivity in detection means sensitivity in detecting patients with a phenotype that is to be detected (that is, the "low responsiveness" phenotype). In other words, the "detection sensitivity" of a certain blood marker may be regarded as the proportion of patients discovered by a prediction method using that blood marker as an indicator, compared to the total number of the patients with the phenotype to be detected. Alternatively, this may be considered the probability of discovering a target patient based on the measured values for that blood marker. Therefore, when detection sensitivity is low, there is an increased probability of overlooking a patient who has a phenotype that should be detected. Patients who are overlooked but should be detected are statistically referred to as false negatives.

Sensitivity in detecting a blood marker is a statistically calculated value. Statistically, there is generally a tradeoff between detection sensitivity and false positives. For example, by setting a low cutoff value, detection sensitivity is increased. However, when a cutoff value is set low, not only detection sensitivity but also noise (false positives) will increase. Herein, noise corresponds to "patients who are responsive". In other words, this means that the number of patients considered to be patients with low responsiveness will increase, even though they are actually responsive. This way, if the cutoff value is lowered, reduced accuracy in prediction is usually unavoidable. Thus, the sensitivity in detecting a marker for detecting a certain phenotype is a statistical value characteristic of that marker.

The present inventors furthered their studies with the objective of improving detection sensitivity in the method for predicting responsiveness based on blood TGFA levels. As a result, the present inventors discovered that by using the blood levels of two markers, TGFA and amphiregulin (AREG), as indicators, detection sensitivity can be greatly improved compared to sensitivity when making predictions using blood TGFA alone, and they thus completed the present invention. Specifically, the present invention relates to the following methods for examining responsiveness to agents for treating lung cancers, methods for treating lung cancers that are based on these examination methods, and reagents or kits for such methods.

[1] a method for treating a lung cancer, which comprises the step of administering an erbB receptor inhibitor to a patient whose blood AREG concentration is low compared to a standard value;

[2] a method for treating a lung cancer, which comprises the step of administering an erbB receptor inhibitor to a patient whose blood AREG concentration or blood TGFA concentration, or both are low compared to standard values;

[3] the method of [2] for treating a lung cancer, which comprises the step of administering an erbB receptor inhibitor to a patient whose blood AREG concentration or blood TGFA concentration is low compared to a standard value;

[4] the therapeutic method of [1], wherein the erbB receptor inhibitor is any compound selected from the group consisting of gefitinib, erlotinib, PKI-166, pelitinib, lapatinib, and canertinib;

[5] a therapeutic agent for a lung cancer comprising an erbB receptor inhibitor as an active ingredient, which is to be administered to a lung cancer patient whose blood AREG concentration is low compared to a standard value;

[6] a therapeutic agent for a lung cancer comprising an erbB receptor inhibitor as an active ingredient, which is to be administered to a lung cancer patient whose blood AREG concentration and blood TGFA concentration are both low compared to standard values;

[7] the therapeutic agent for lung cancer of [5] or [6], wherein the erbB receptor inhibitor is any compound selected from the group consisting of gefitinib, erlotinib, PKI-166, pelitinib, lapatinib, and canertinib;

[8] a use of an erbB receptor inhibitor for the production of a therapeutic agent for a lung cancer to be administered to a lung cancer patient whose blood AREG concentration and blood TGFA concentration are both low compared to standard values;

[9] a kit for treating a lung cancer, comprising the following elements:

(1) a therapeutic agent for a lung cancer comprising an erbB receptor inhibitor as an active ingredient; and (2) an instruction sheet stating that a patient whose blood AREG concentration is high compared to a standard value has low responsiveness to a therapeutic agent for a lung cancer comprising an erbB receptor inhibitor as an active ingredient;

[10] the kit of [9] for treating a lung cancer, which additionally comprises the following element:

(3) an instruction sheet stating that a patient whose blood TGFA concentration is high compared to a standard value has low responsiveness to a therapeutic agent for a lung cancer comprising an erbB receptor inhibitor as an active ingredient;

[11] a method for examining the responsiveness to a therapeutic agent for a lung cancer comprising an erbB receptor inhibitor as an active ingredient, wherein the method comprises the steps of:

(1) measuring AREG concentration in a blood sample of a lung cancer patient; and (2) determining that responsiveness of the patient to a therapeutic agent for a lung cancer comprising an erbB receptor inhibitor as an active ingredient is low, when the AREG concentration is high compared to a standard value;

[12] the examination method of [11], which additionally comprises the steps of:

(1) measuring the TGFA concentration in a blood sample of a lung cancer patient; and (2) determining that responsiveness of the patient to a therapeutic agent for a lung cancer comprising an erbB receptor inhibitor as an active agent is low, when the AREG concentration or the TGFA concentration or both are higher than standard values;

[13] the method of [11], wherein the responsiveness of the patient to a therapeutic agent for a lung cancer comprising an erbB receptor inhibitor as an active agent is determined to be low, when the AREG concentration or TGFA concentration is high compared to a standard value;

[14] the examination method of [11], which comprises measuring the AREG concentration of a blood sample using an immunoassay;

[15] a kit for examining responsiveness to a therapeutic agent for a lung cancer comprising an erbB receptor inhibitor as an active ingredient, wherein the kit comprises the following elements:

i. an immunoassay reagent for measuring a blood concentration of AREG; and ii. a positive control for AREG;

[16] the kit for examination of [15], which additionally comprises the following elements:

iii. an immunoassay reagent for measuring a blood concentration of TGFA; and iv. a positive control for TGFA;

[17] the kit for examination of [16], wherein a sample for the positive control comprises both AREG and TGFA; and

[18] the kit for examination of [17], wherein the sample for the positive control is a liquid.

The present invention provided methods for predicting responsiveness to erbB receptor inhibitors based on blood markers. Blood markers can be measured conveniently and economically using blood as a sample. They can also be evaluated quantitatively by techniques such as immunoassays. Further, in the present invention, detection sensitivity for patients whose responsiveness is low is improved significantly by using AREG as a second marker in addition to the known marker TGFA.

In addition, the present invention provided methods for treating lung cancers, where the methods comprise the step of administering an erbB receptor inhibitor to patients predicted by the present invention to be responsive to an erbB receptor inhibitor. Gefitinib and such are included as erbB receptor inhibitors. Gefitinib is a pharmaceutical agent considered desirable for administration to selected patients expected to be as responsive as possible to the agent. The present invention enables highly sensitive detection of patients with low responsiveness, and specific selection of patients expected to be responsive. As a result, it may dramatically improve the therapeutic benefits of the methods for treating lung cancers using erbB receptor inhibitors such as gefitinib.

The present invention can also prevent the risk of unnecessary side effects that accompany administration of pharmaceutical agents to patients who cannot be expected to respond. Side effects caused by drugs that cannot be expected to show therapeutic benefits will significantly damage a patient's quality of life (QOL). Generally, therapeutic intervention for diseases, including the administration of pharmaceutical agents, is accompanied by the risk of side effects to varying degrees. Therefore, the fundamental principle of medical care is the selection of therapeutic methods believed to yield the greatest therapeutic benefits by considering the risk of side effects and the expected therapeutic benefits. Medical practices not expected to be therapeutically beneficial should not be selected. Therefore, the ability to predict which patients will have low responsiveness will lead to improvements in quality of life for lung cancer patients.

TGFA and AREG are both EGFR ligands whose expression levels in lung cancer tissues have been indicated to be associated with responsiveness to gefitinib. In addition, the level of blood TGFA has been shown to be associated with responsiveness to gefitinib. However, there have been no reports that the blood level of AREG can be a predictive marker for responsiveness to erbB receptor inhibitors. Furthermore, the discovery that the sensitivity of detection of patients with low responsiveness can be significantly improved by combining the predictive results of TGFA and AREG, as compared to when predictions are made with TGFA alone, was a finding beyond expectation. Specifically, the combined use of AREG enables the detection of 50% or more of the patients who could not be detected using predictions from blood TGFA. In other words, measuring AREG can pick up more than half of the patients who are overlooked by TGFA measurements but who actually have low responsiveness.

In more detail, for example, data from the Examples below shows detection sensitivity for TGFA and AREG as 43.3% and 40%, respectively. This result shows that over 40% of patients with low responsiveness can be discovered by measuring these markers. The present inventors analyzed each of the TGFA-positive patients and AREG-positive patients in more detail. They discovered that the two do not overlap completely. That is, by using the two markers TGFA and AREG as indicators, each marker made up for the other in catching patients overlooked when using the markers individually. As a result, ultimately, another 50% or more of the patients who are overlooked when each of the markers were used individually could be newly detected.

Furthermore, in a preferred embodiment of the present invention, PD cases can be distinguished from PR or SD patients. In contrast, known methods for analyzing EGFR mutations could select PR patients, but it was almost impossible to recognize SD patients. This is one of the important advantages of the present invention.

BEST MODE FOR CARRYING OUT THE INVENTION

Figure 1:
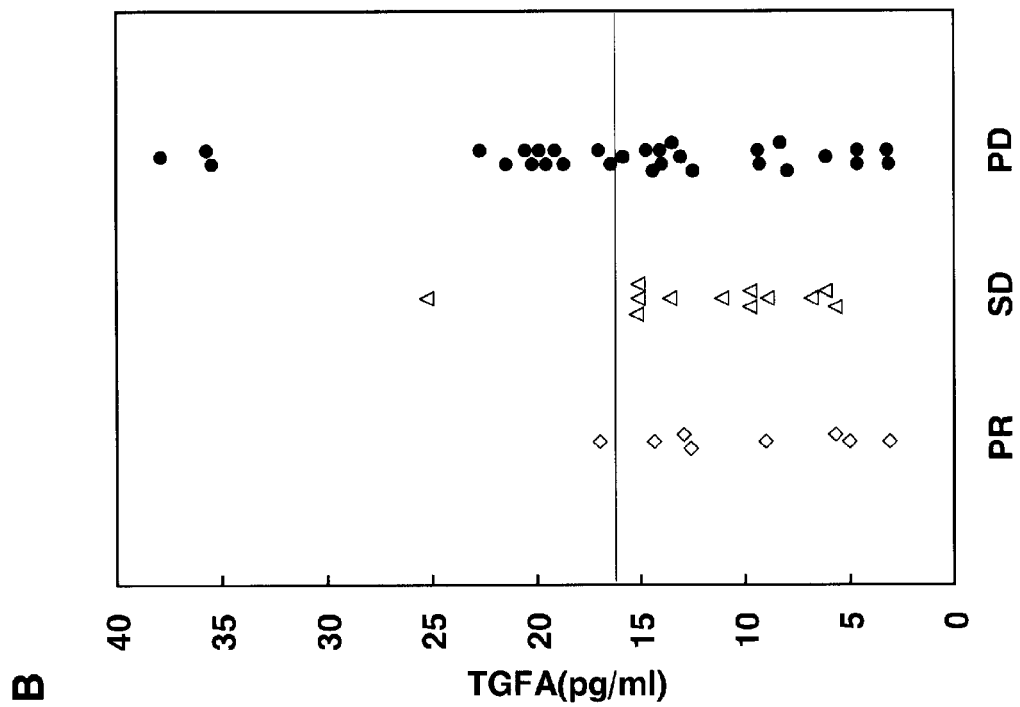
FIG. 1 shows the results of ELISA measurements of the concentrations of amphiregulin (AREG; A) and TGFA (TGFA; B) in serum from 50 NSCLC patients treated with gefitinib therapy. Eight cases were PR, twelve were SD, and 30 were PD. Horizontal lines indicate cutoff levels; positivity was indicated for concentrations above the lines, and negativity was indicated for those below the lines.
Figure 1:
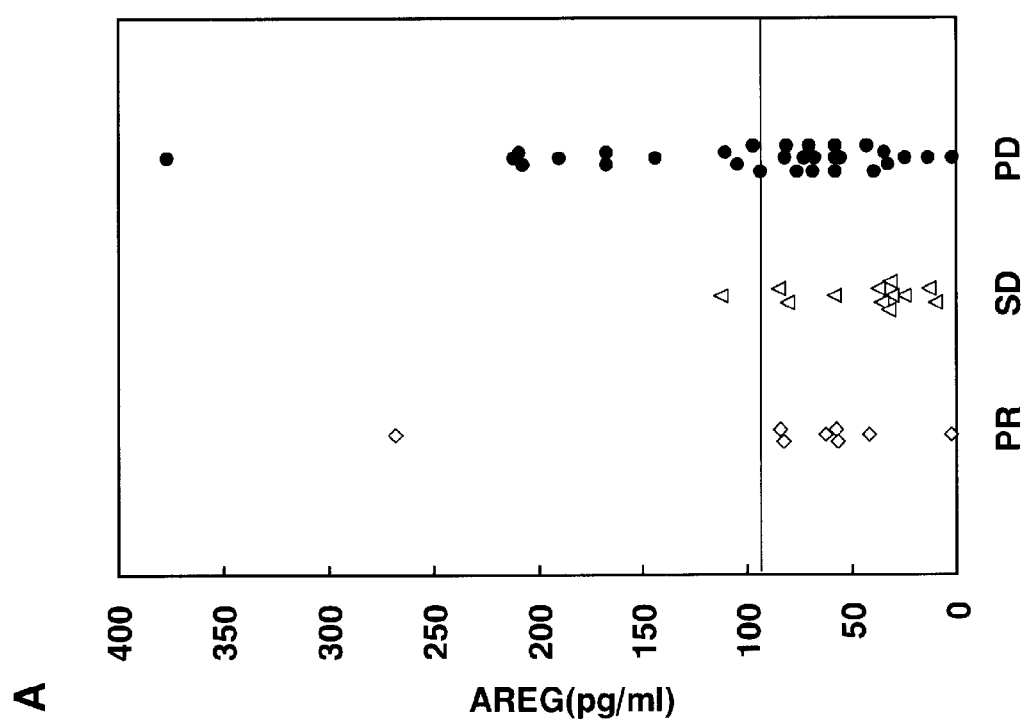

Tyrosine kinase receptors belonging to the erbB family have been found to be closely associated with cell growth and survival of cancer cells. Known examples of these types of receptors include erbB2, erbB3, erbB4, or EGFR (Klapper L N. et al., Adv. Cancer Res. 2000, 77:25-79). In cancers with high levels of expression of these receptors, a tendency towards high activity and poor prognosis has been observed. In contrast, cell growth was found to be suppressed upon inhibiting erbB expression or activity (Mendelsohn et al., Oncogene 2000, 19, 6550-65). Based on these findings, the development of inhibitors for tyrosine kinase receptors belonging to the erbB family as anticancer agents was pursued. Gefitinib is a compound discovered through such a process.

In the present invention, erbB receptor inhibitors refer to compounds with the effect of suppressing the activity of tyrosine kinase receptors belonging to the erbB family. Therefore, for example, inhibitors against erbB2, erbB3, erbB4, or EGFR activity are included in the erbB receptor inhibitors of the present invention.

erbB receptor inhibitors may be compounds that act specifically against a particular receptor, or compounds that act against a number of receptors. In the present invention, inhibition of receptor activity refers to suppression of any stage in the function of a receptor that transduces signals to cells via ligand binding. Therefore, antagonists that inhibit binding between a ligand and receptor are representative erbB receptor inhibitors. Alternatively, compounds that have inhibitory activity against a tyrosine kinase activity necessary for signal transduction are also included in the erbB receptor inhibitors. For example, gefitinib is orally administered to inhibit the growth of cancer cells by blocking signal transduction via EGFR receptors in vivo.

More specifically, for example, compounds such as the following may be indicated as the erbB receptor inhibitors of the present invention. These compounds can also be administered as pharmaceutically acceptable salts. The preferred erbB receptor inhibitor in the present invention is gefitinib.
Gefitinib:
N-(3-chloro-4-fluorophenyl)-7-methoxy-6-(3-morpholinopropoxy)quinazolin-4-amine); (Gefitinib; ZD1839, Chemical Abstracts Registry Number 184475-25-2, product name "Iressa", Woodburn, J. R., et al.: Proc. Am. Assoc. Cancer Res., 38, 633 Abs 4251, 1997; Pharmacol. Ther., 1999, 82, 241-250)
Erlotinib:
N-(3-ethynylphenyl)-6,7-bis(2-methoxyethoxy)quinazolin-4-amine; (Erlotinib, OSI-774, Chemical Abstracts Registry Number 183319-69-9, product name "Tarceva" WO 99/55683)
Development Code PKI-166:
4-[(1R)-1-phenylethylamino]-6-(4-hydroxyphenyl)-7H-pyrrolo[2,3-d]pyrimidine; (PKI-166, WO 97/02266)
Pelitinib:
2-Butenamide,
N-(4-((3-chloro-4-fluorophenyl)amino)-3-cyano-7-ethoxy-6-quinolinyl)-4-(dimethylamino)-, (2E)-; (Pelitinib; EKB-569, Chemical Abstracts Registry Number 257933-82-7, Torrance C J, et al., Nature Med. 2000, 6, 1024-1028, U.S. Pat. No. 6,002,008)
Lapatinib:
N-(3-chloro-4-(((3-fluorobenzyl)oxy)phenyl)-6-(5-(((2-methylsulfonyl)ethyl)amino)methyl)-2-furyl)-4-quinazolinamine; (Lapatinib, GW572016, Chemical Abstracts Registry Number 231277-92-2, WO 99/35146, WO 01/04111)
Canertinib:
2-Propenamide, N-(4-((3-chloro-4-fluorophenyl)amino)-7-(3-(4-morpholinyl)propoxy)-6-quinazolinyl); (Canertinib; CI-1033, Chemical Abstracts Registry Number 289499-45-2, Smaill J B, et al., J. Med. Chem. 1999, 42, 1803-15, WO 00/31048)

Patients are generally regarded as being responsive to a therapeutic agent when their tumor, which constitutes the cancerous lesion to be treated, is confirmed to degenerate after administration of a therapeutic agent for lung cancer comprising an erbB receptor inhibitor as an active ingredient. In contrast, patients are regarded as being non-responsive when their tumor cannot be confirmed to degenerate after administration of the therapeutic agent. Several criteria for comparing the degree of responsiveness have been established. Responsiveness in the present invention can be determined, for example, based on criteria for comparison of responsiveness to these known anticancer agents.

In the 1970s, the International Union Against Cancer (UICC) proposed criteria for assessing the effectiveness of antitumor agents (Eur. J. Cancer 13: 89-94, 1977). The World Health Organization (WHO) also recommended this rating system (WHO offset Publication No. 48, 1979). The rating system by WHO presents representative criteria for responsiveness (Miller A B et al., Cancer 1981; 47:207-14). Later, cases in which patients were erroneously found to be PD were pointed out as issues for the WHO guidelines. Therefore, research groups such as the Southwest Oncology Group (SWOG) developed new guidelines (Green S and Weiss G R., Invest. New Drugs 1992; 10:239-53). In the guidelines developed by Green and Weiss, the main revisions were to the criteria for PD.

Based on these criteria, the RECIST (Response Evaluation Criteria in Solid Tumors Group) guidelines were also newly established and are another of the representative evaluative criteria (Therasse P, et al., J. Natl. Cancer. Ins. 2000, Vol. 92, No. 3, 205-16). The main difference between the WHO guidelines and the RECIST guidelines lies in the method for measuring tumor size. In the WHO guidelines, the effectiveness of an anticancer agent is determined based on the change in the sum of the tumor volumes (two-dimensional information). On the other hand, in the RECIST guidelines, effectiveness is determined based on the sum of the maximal tumor diameters (one-dimensional information). These guidelines are summarized in Table 1.

TABLE 1

| | WHO | RECIST |
| --- | --- | --- |
| CR | Disappearance (confirmed after four weeks) | Disappearance (confirmed after four weeks) |
| PR | 50% decrease (confirmed after four weeks) | 30% decrease (confirmed after four weeks) |
| SD | Neither PR nor PD criteria met | Neither PR nor PD criteria met |
| PD | 25% increase (Provided that PD was not judged to be CR, PR, or SD prior to the increase in lesions) | 20% increase |

CR: Complete Response
PR: Partial Response
SD: Stable Disease; also denoted as No Change
PD: Progressive Disease In practice, in addition to criteria for effectiveness based on change in tumor size, these guidelines point out various important matters, such as those below, which are necessary for determining therapeutic benefits. In all events, those skilled in the art can objectively determine the responsiveness of patients to certain anticancer agents based on such known guidelines.
  Statistical criteria
  Standard methods for measuring tumor tissues
  Measurement of tumor markers
  Histological examinations
  Methods for recording the results of examinations
  Evaluation of non-target tissues The responsiveness of lung cancer patients to therapeutic agents for lung cancers that comprise erbB receptor inhibitors as active ingredients can be predicted with high precision by using scoring systems that use the expression levels of several marker genes in lung cancer tissues as indicators (Kakiuchi S, et al., Hum. Mol. Genet. 2004; 13:3029-43.; WO 2005/49829). However, lung cancer tissues are not always easy to collect. Further, time-consuming and sophisticated analytical techniques are required to quantitatively determine the expression levels of a number of genes in lung cancer tissues. Therefore, in these reports, the relationship between blood TGFA concentration and responsiveness was examined. Blood TGFA concentration measurements showed that patients with low responsiveness can be screened to some degree. However, the detection sensitivity was less than 50%. The present inventors showed that by using blood AREG concentration as an indicator, patients with low responsiveness can be found with high detection sensitivity, and they thus completed the present invention.

The present invention relates to methods for treating lung cancers, where the methods comprise the step of administering an erbB receptor inhibitor to a patient whose blood AREG concentration is low compared to a standard value.

In the present invention, blood concentration refers to the concentration of a substance present in the blood after correcting for the volume of blood cells constituting the whole blood. The percentage of blood cell volume constituting the blood varies greatly among individuals. For example, the percentage of red blood cells in whole blood is very different between men and women. Further, differences between individuals cannot be ignored. Therefore, the apparent concentration of substances in whole blood including blood cell components varies greatly depending on the percentage of blood cell volume. For example, even if the concentration in serum is the same, the measured value for a sample containing large amounts of blood cell components will be lower than the value for a sample containing smaller amounts of blood cell components. Therefore, to compare measured blood component values, values corrected for the volume of blood cells are ordinarily used.

Measured values free from the influence of blood cell volume can be obtained by, for example, using serum or plasma, obtainable by separating blood cells from whole blood, as samples for measuring blood components. Therefore, ordinarily, blood concentration in the present invention can be determined as a concentration in serum or plasma. Alternatively, the influence of the volume of blood cells may be corrected after measuring the concentration in whole blood. Methods for measuring the volume of blood cells constituting a whole blood sample are well known.

In the present invention, blood AREG concentration can be associated with responsiveness to erbB receptor inhibitors by comparison to standard values. A standard value is a numerical value that will serve as a criterion for determining whether a test subject is responsive. Standard values are also called cutoff values. In the present invention, patients whose blood AREG concentration is high are determined to have low responsiveness to erbB receptor inhibitors. In general, values that enable separation of those that have and do not have characteristics to be assessed can be used as standard (cutoff) values. In the present invention, a characteristic to be assessed is responsiveness to an erbB receptor inhibitor. Therefore, the standard values are associated with responsiveness to erbB receptor inhibitors. Specifically, the present invention relates to a method for treating lung cancers, which comprises the following steps of:

(1) measuring the blood AREG concentration in lung cancer patients;
(2) comparing the values measured in step (1) with the blood AREG concentration measured for patients who are responsive to an erbB receptor inhibitor; and
(3) as a result of the comparison in step (2), administering the erbB receptor inhibitor to patients for whom the value measured in step (1) is the same level as the value measured for patients confirmed to be responsive to the erbB receptor inhibitor.

In a preferred embodiment of the present invention, in the aforementioned step (3), for example, patients expected to be determined to be either CR or PR may be selected as patients who should be administered with an erbB receptor inhibitor. Specifically, the present invention allows the administration of an erbB receptor inhibitor to be avoided for patients likely to be determined as PD, regardless of whether an erbB receptor inhibitor was administered. CR, PR, SD, and PD mentioned herein can be determined, for example, based on the following criteria. The criteria for CR, PR, SD, and PD are determined according to the aforementioned criteria of WHO or Green et al., or the RECIST guidelines.

Complete response (CR): patients judged to be CR at two treatments carried out with an interval of at least 28 days;

Partial Response (PR): patients judged to be PR or showing better effects at two treatments carried out with an interval of at least 28 days;

Stable Disease (SD): patients judged to be SD or showing better effects at two treatments carried out with an interval of least 28 days, but who were not CR or PR. SD is first assessed at a tumor assessment point 28 days or more after the start of medication treatment;

Progressive Disease (PD): patients who were determined to be PD at or before the first tumor assessment point, which is 28 days after the start of medication treatment.

In the present invention, patients whose blood AREG concentration is low compared to a standard value can be selected by the aforementioned steps (2) and (3), for example. Specifically, first, the AREG values measured for patients whose responsiveness is to be determined (subjects) are compared with the blood AREG concentration values measured for patients who were responsive to an erbB receptor inhibitor (control). If a value measured for a subject is at the same level as that of the control, this indicates that the subject is an aforementioned patient whose blood AREG concentration is low compared to a standard value. In a preferred embodiment of the present invention, patients who are responsive to an erbB receptor inhibitor include patients who are determined to be CR or PR. Patients whose responsiveness is low include patients determined to be PD.

Blood concentrations of AREG can be found to be at the same level using statistical comparison. For example, the blood AREG concentration of a number of patients who are responsive to an erbB receptor inhibitor can be measured to statistically determine the standard blood AREG concentration. When a statistically sufficient population can be gathered, values within the range of twice the standard deviation (S.D.) from the mean value are often used as standard values. Therefore, values corresponding to the mean value+2×S.D. may be used as standard values. Standard values established in this way theoretically include 90% of the patients determined to be CR or PR.

Alternatively, for patients who have actually been administered an erbB receptor inhibitor, responsiveness can be determined according to the above-mentioned criteria, and standard values can be set based on their blood AREG concentration. Ordinarily, standard values set this way minimize the false positive ratio, and are selected within a range satisfying conditions that can maximize detection sensitivity. Herein, a false-positive ratio refers to the percentage of patients determined to be CR or PR and whose blood AREG concentration is determined to be higher than a standard value. Conversely, specificity is indicated by the proportion of patients determined to be either CR or PR and whose blood AREG concentration is determined to be lower than a standard value. That is, the sum of the false-positive ratio and specificity is always 1. Detection sensitivity refers to the percentage of patients whose blood AREG concentration is judged to be higher than a standard value out of all patients determined to be either PD or SD.

Furthermore, in the present invention, the percentage of SD or PD patients from among patients whose AREG concentration has been judged to be higher than a standard value is referred to as a positive predictive value. Conversely, the percentage of CR or PR patients from among patients whose AREG concentration has been judged to be lower than a standard value is referred to as a negative predictive value. The relationship between these values is summarized in Table 2. As the following relationships show, each of the values for sensitivity, specificity, positive predictive value, and negative predictive value, which are indicators for evaluating the prediction accuracy for responsiveness, all vary depending on the standard value for judging the level of blood AREG concentration.

TABLE 2

| Blood AREG concentration | SD + PD patients | CR + PR patients | |
|---|---|---|---|
| High | a: True positive | b: False positive | Positive predictive value a/(a + b) |
| Low | c: False negative | d: True negative | Negative predictive value d/(c + d) |
| | Sensitivity a/(a + c) | Specificity d/(b + d) | |

As already mentioned, a standard value is ordinarily set such that the false positive ratio is low and sensitivity is high. However, as is clear from the relationships above, there is a tradeoff between the false positive ratio and sensitivity. That is, if the standard value is decreased, detection sensitivity will be increased. However, since this also increases the false positive ratio, satisfying the "low false positive ratio" condition becomes difficult. Considering this situation, for example, numerical values that give anticipated results such as the following may be selected as preferred standard values in the present invention:

A standard value such that the false positive ratio is 50% or less (that is, a standard value such that specificity is 50% or higher)

A standard value such that sensitivity is not less than 20%

In the present invention, a standard value can be set using an ROC curve. A receiver operating characteristic (ROC) curve is a graph showing detection sensitivity on the vertical axis, and the false positive ratio on the horizontal axis (that is, "1—specificity"). In the present invention, a ROC curve can be obtained by plotting the changes in sensitivity versus false positive ratio observed when continuously varying the standard value for determining whether a blood AREG concentration is high or low.

A "standard value" used for obtaining an ROC curve is a numerical value used temporarily for statistical analyses. A "standard value" for obtaining an ROC curve is generally continuously varied within a range that can cover all standard values that may be selected. For example, a standard value can be varied between the smallest and largest values measured for AREG in the population to be analyzed.

Based on an obtained ROC curve, a suitable standard value for use in the present invention may be selected within a range satisfying the above-mentioned conditions. Alternatively, a standard value can be selected based on an ROC curve produced by varying the standard value in a range that includes most of the measured AREG values. More specifically, for example, in the group of patients analyzed by the present inventors, the relationship between the cutoff value, false positive ratio, and sensitivity can be summarized as below. The ROC curves of FIG. 2 can be obtained by plotting the following values on a graph.

AREG

| Cutoff value (pg/mL) | False positive ratio; Sensitivity |
|---|---|
| 50 | 50%; 73.3% |
| 70 | 30%; 53.5% |
| 80 | 25%; 43.3% |
| 85 | 10%; 40% |
| 90 | 10%; 36.7% |
| 93.8 | 10%; 36.7% |
| 95 | 10%; 36.7% |
| 100 | 10%; 33.3% |
| 110 | 10%; 26.7% |
| 130 | 5%; 23.3% |
| 150 | 5%; 23.3% |
| 155.219 | 5%; 20% |

TGFA

| Cutoff value (pg/mL) | False positive ratio; Sensitivity |
|---|---|
| 10 | 50%; 70% |
| 11 | 45%; 70% |
| 12 | 45%; 66.7% |
| 13 | 35%; 63.3% |
| 13.5 | 35%; 60% |
| 14 | 30%; 53.3% |
| 14.5 | 25%; 50% |
| 15 | 15%; 46.7% |
| 15.5 | 10%; 43.3% |
| 16 | 10%; 43.3% |
| 17 | 5%; 36.7% |
| 18 | 5%; 33.3% |
| 19 | 5%; 30% |
| 20 | 10%; 43.3% |
| 21 | 5%; 20% |

Therefore, based on the ROC curve, standard values that yield a false positive ratio of 50% or less and a sensitivity of 20% or more can be shown to be 56.306 pg/mL to 155.219 pg/mL.

Alternatively, standard values that satisfy conditions such as the following may be employed using positive predictive value and negative predictive value as indicators.

Standard values that yield positive predictive value of 60% or more

Standard values that yield negative predictive value of 40% or more

In the present invention, patients whose blood AREG concentration is to be measured to determine a standard value can be chosen from patients who have been administered an erbB receptor inhibitor for the purpose of lung cancer therapy. Many erbB receptor inhibitors that are commercially available or pharmaceutical agents for which clinical trials have started are known. Therefore, blood samples can be collected after obtaining the consent of patients who were administered such pharmaceutical agents. Furthermore, by associating the therapeutic outcomes of patients whose blood sample was collected with the blood concentration of AREG, standard values can be set according to a method such as that described above.

The patients whose blood AREG concentration is measured to set a standard value are preferably a population of patients considered to be representative of a population of patients who should be treated by the present invention. More specifically, for example, in the present invention it is preferable to have set standard values for each ethnic group.

In the treatment methods of the present invention, as part of selecting patients who should be administered an erbB receptor inhibitor, the blood TGFA concentration may be referred to in addition to the AREG blood concentration. More specifically, the present invention relates to methods for treating lung cancers, wherein the methods comprise the step of administering an erbB receptor inhibitor to patients whose blood AREG concentration or blood TGFA concentration or both are low compared to standard values. Alternatively, the present invention relates to methods for treating lung cancers, wherein the methods comprise the step of administering an erbB receptor inhibitor to patients whose blood AREG concentration or blood TGFA concentration is low compared to standard values.

Alternatively, the present invention relates to therapeutic agents for lung cancers that comprise erbB receptor inhibitors as active ingredients, which are to be administered to lung cancer patients whose blood AREG concentration is low compared to a standard value. As already mentioned, patients whose responsiveness to an erbB receptor inhibitor is low can be detected with higher sensitivity by combining the values measured for blood AREG concentration and blood TGFA concentration. More specifically, in the present invention, patients whose measured values of both blood AREG and TGFA are lower than cutoff values are a preferred group of patients as subjects for administering a therapeutic agent for lung cancer comprising an erbB receptor inhibitor as an active ingredient. Therefore, the present invention provides pharmaceutical agents for lung cancer comprising an erbB receptor inhibitor as an active ingredient, which are to be administered to lung cancer patients whose blood AREG concentration and blood TGFA concentration are both low compared to standard values.

Furthermore, the present invention relates to uses of erbB receptor inhibitors in the production of therapeutic agents for lung cancers, which are to be administered to lung cancer patients whose blood AREG concentration is low compared to a standard value. Further, the present invention also relates to uses of erbB receptor inhibitors in the production of pharmaceutical agents for lung cancers, which are to be administered to lung cancer patients whose blood AREG concentration and blood TGFA concentration are both low compared to standard values.

An active ingredient in the therapeutic agents of the present invention for lung cancers is an erbB receptor inhibitor. Preferred erbB receptor inhibitors are gefitinib, erlotinib, PKI-166, pelitinib, lapatinib, and canertinib.

Responsiveness to an erbB receptor inhibitor is already known to be predictable using blood TGFA concentration. The present invention further showed that by newly combining an evaluation using the measured values for AREG, the predictive accuracy for responsiveness based on separate measurements of TGFA or AREG alone can be improved. More specifically, the present invention provides methods for treating lung cancers by predicting responsiveness to erbB receptor inhibitors using two factors—TGFA and AREG—as indicators. Alternatively, the present invention provides therapeutic agents for lung cancers, which are to be administered to certain lung cancer patients who have been screened based on their blood concentrations of TGFA and AREG.

Specifically, for example, a subject is shown to be unresponsive to erbB receptor inhibitors when the two factors, blood TGFA and AREG, are measured, and either one of them exceeds their respective standard value. In other words, based on the present invention, lung cancer patients whose blood concentrations of TGFA and AREG are both lower than standard values will be determined to be responsive to erbB receptor inhibitors. The present invention can greatly improve the sensitivity of detection of patients who are unresponsive to an erbB receptor inhibitors as compared to evaluations based on the results of measuring TGFA alone. Behind this improvement is the fact that the group of TGFA-positive patients and the group of AREG-positive patients do not completely overlap. This will be described in more detail:

First, a certain percentage of patients whose result measured for TGFA values are lower than standard values (those responsive to erbB receptor inhibitors), are in fact non-responsive. Such patients are regarded as TGFA-false-negative patients. By combining an evaluation based on TGFA with an evaluation based on AREG, patients whose AREG level is above standard values can be found among the TGFA-false-negative patients. That is, the present invention can be used to find patients who are in fact non-responsive from among those patients erroneously evaluated as "responsive" due to a low blood TGFA concentration. In this way the present invention improved the sensitivity of detection of patients who are not responsive to erbB receptor inhibitors. Generally, although simply combining the results of evaluations from multiple markers can increase detection sensitivity, this often leads simultaneously to a reduction in specificity. However, by determining the best balance between sensitivity and specificity, the present invention has elucidated a characteristic combination that can increase detection sensitivity without compromising specificity.

In the present invention, erbB receptor inhibitors can be administered to patients whose TGFA and AREG values are both less than standard values. Selecting patients for whom the two values do not exceed standard values can increase the proportion of patients who are responsive.

In the present invention, in order to inclusively consider the results of TGFA measurements, for example, the blood concentration of TGFA can be measured, and then compared to a standard value, just as in the aforementioned comparison between measured and standard AREG values. For example, there are already reports on measuring the blood TGFA concentration and comparing it to standard values (Kakiuchi S, et al., Hum. Mol. Genet. 2004; 13:3029-43.; WO 2005/49829). An ELISA kit for TGFA is also commercially available. These methods described in publicly known reports can be used in the methods of the present invention for treating lung cancers using erbB receptor inhibitors.

AREG (amphiregulin) in the blood, which is measured in the present invention, is a protein also called schwannoma-derived growth factor. One of the more than 15000 genes isolated as a result of the National Institutes of Health Mammalian Gene Collection (MGC) Program was a gene coding for AREG (Strausberg R L, et al., Proc. Natl. Acad. Sci. USA. 2002 Dec. 24; 99(26):16899-903). AREG is considered to be an autocrine growth factor and a member of the epithelial growth factor family. Specifically, it binds to EGF/TGF-alpha receptor and brings about cell growth. Conversely, it is also known to show growth inhibitory effects against certain highly malignant epithelial carcinoma cell lines.

Blood AREG can be measured by any method that can quantify proteins. For example, immunoassays, liquid chromatography, surface plasmon resonance (SPR), or mass spectrometry may be applied as methods for quantifying proteins. In mass spectrometry, proteins can be quantified using suitable internal standards. Isotope-labeled AREG and such may be used as internal standards. Blood AREG concentration can be determined from the peak intensities of blood AREG and an internal standard. Generally, for mass spectrometry of proteins, a matrix-assisted laser desorption/ionization method (MALDI) is used. An analysis method using mass spectrometry or liquid chromatography can simultaneously analyze AREG and TGFA.

Immunoassays are preferred method for measuring AREG in the present invention. The amino acid sequence of AREG is publicly known (Genbank Accession Number BC009799). The amino acid sequence of an AREG is shown in SEQ ID NO: 2, and the nucleotide sequence of a cDNA encoding it is shown in SEQ ID NO: 1. Therefore, those skilled in the art can prepare antibodies by synthesizing a necessary immunogen based on the amino acid sequence of AREG Peptides that will serve as immunogens can be synthesized easily using peptide synthesizers. The synthetic peptides can be made into immunogens by linking them to carrier proteins.

Keyhole limpet hemocyanin, myoglobin, albumin, and such may be used as carrier proteins. Preferred carrier proteins include KLH and bovine serum albumin. The maleimidobenzoyl-N-hydrosuccinimide ester method (hereinafter abbreviated as the MBS method), and such are generally used to link synthetic peptides to carrier proteins.

Specifically, a cysteine is introduced into a synthetic peptide, and the peptide is cross-linked to KLH using the cysteine's SH group according to the MBS method. The cysteine residue may be introduced at the N terminus or C terminus of the synthesized peptide.

Alternatively, AREG can also be obtained as a genetic recombinant based on the nucleotide sequence of AREG (Genbank Accession Number BC009799). DNAs comprising a necessary nucleotide sequence can be cloned using mRNAs prepared from AREG-expressing tissues. Commercially available cDNA libraries can also be used as cloning sources. The obtained genetic recombinants of AREG, or fragments thereof may be used as immunogens. AREG recombinants expressed in this manner are preferred immunogens for use in obtaining antibodies in the present invention. Alternatively, commercially available AREG recombinants (R & D Systems, Product No: 262-AR-100) may also be used as immunogens.

Immunogens obtained in this manner are mixed with suitable adjuvants, and used to immunize animals. Known adjuvants include Freund's complete adjuvant (FCA) and incomplete adjuvant. The immunization is repeated with appropriate intervals until an increase in antibody titer is confirmed. There are no particular limitations on the animals to be immunized in the present invention. Specifically, mice, rats, rabbits, or such animals commonly used for immunization may be used.

When obtaining the antibodies as monoclonal antibodies, animals that are advantageous for producing them may be used. For example, in mice, many myeloma cell lines for cell fusion are known, and techniques capable of establishing hybridomas with a high probability have already been developed. Therefore, mice are one of the preferable animals for immunization to obtain monoclonal antibodies.

Furthermore, immune treatments are not limited to in vivo treatments. Methods for immunologically sensitizing cultured immunocompetent cells in vitro can also be employed. Antibody-producing cells obtained by these methods are transformed and cloned. The methods for transforming antibody-producing cells to obtain monoclonal antibodies are not limited to cell fusion. For example, methods for obtaining clonable transformants through viral infection are known.

Hybridomas that produce monoclonal antibodies for use in the present invention can be screened based on their reactivity to AREG. Specifically, antibody-producing cells are first selected by using, as an indicator, their binding activities toward AREG or its domain peptides, which were used as antigens. Positive clones selected by this screening are subcloned as necessary.

After culturing the established hybridomas under suitable conditions, produced antibodies are collected to yield monoclonal antibodies to be used in the present invention. When the hybridomas are homohybridomas, they can be cultured in vivo by inoculating them intraperitoneally to syngeneic animals. In this case, monoclonal antibodies are collected as peritoneal fluid. When heterohybridomas are used, they can be cultured in vivo using nude mice as a host.

In vivo culturing, as well as in vitro culturing of hybridomas in appropriate culture environments are generally conducted. For example, basal media such as RPMI 1640 and DMEM are generally used as the media for hybridomas. Animal serum and such additives can be added to these media to maintain the antibody producing ability at a high level. When hybridomas are cultured in vitro, monoclonal antibodies can be collected as a culture supernatant. The culture supernatant can be collected by separating it from cells after culturing, or, when using a culturing apparatus that applies hollow fibers, it can be continuously collected while culturing.

Monoclonal antibodies collected as peritoneal fluid or culture supernatants are prepared into monoclonal antibodies used in the present invention by separating the immunoglobulin fraction by saturated ammonium sulfate precipitation followed by purification steps including gel filtration and ion exchange chromatography. In addition, if the monoclonal antibodies are IgGs, purification methods based on affinity chromatography with a protein A or protein G column are effective.

On the other hand, to obtain the antibodies for use in the present invention as polyclonal antibodies, blood is drawn from individuals whose antibody titer increased after immunization, and the serum is separated to obtain anti-serum. Immunoglobulins are purified from the anti-serum by known methods to prepare the antibodies to be used in the present invention. If immunoaffinity chromatography using AREG as a ligand is used in combination with immunoglobulin purification, AREG-specific antibodies can be obtained.

The following commercially available antibodies can be combined and used in measurements of the present invention. For example, monoclonal antibodies such as the following are marketed as products:

Anti-human Amphiregulin Antibody (R & D Systems, Catalog No: MAB262): this product is a monoclonal antibody derived from mouse-mouse hybridomas obtained using an *E. coli*-derived AREG recombinant as the immunogen.

Alternatively, polyclonal antibodies such as the following are also commercially available:

Anti-human Amphiregulin Antibody (R & D Systems, Catalog No: AB-262-NA): this product is a polyclonal antibody obtained by immunizing goats with an *E. coli*-derived AREG recombinant.

Biotinylated Anti-human Amphiregulin Antibody (R & D Systems, Catalog No: BAF262): this product is an antibody obtained by biotinylating a polyclonal antibody obtained by immunizing goats with an *E. coli*-derived AREG recombinant.

When antibodies against AREG contact AREG, the antibodies bind to the antigenic determinants (epitopes) recognized by the antibodies through the antigen-antibody reaction. The binding of antibodies to antigens can be detected using various immunoassay principles. Immunoassays can be broadly categorized into heterogeneous analysis methods and homogeneous analysis methods. The use of monoclonal antibodies is preferable to maintain high levels of sensitivity and specificity for the immunoassays. The methods of the present invention for measuring AREG using a variety of immunoassay formats will be described in detail below.

First, methods for measuring AREG using heterogeneous immunoassays will be described. In heterogeneous immunoassays, mechanisms for separately detecting AREG-bound and AREG-unbound antibodies are required.

To facilitate separation, immobilized reagents are generally used. For example, first, a solid phase onto which antibodies recognizing AREG have been immobilized is prepared (immobilized antibodies). AREG is bound to this, and then further reacted with a second labeled antibody.

When the solid phase is separated from the liquid phase and then washed as necessary, a certain amount of second antibody proportional to the concentration of AREG remains on the solid phase. By labeling the second antibody, AREG can be quantified by measuring the signal which comes from this label.

Any method may be used to bind the antibodies to the solid phase. For example, antibodies can be physically adsorbed to hydrophobic materials such as polystyrene. Alternatively, antibodies can be chemically bound to a variety of materials having functional groups on their surfaces. Furthermore, antibodies labeled with a binding ligand thereof can be bound to a solid phase by trapping the ligand with its binding partner. Combination of a binding ligand and its binding partner includes the avidin-biotin combination or such. The solid phase and antibodies can be conjugated at the same time when reacting the second antibody, or after this reaction.

Similarly, labeling of the second antibody does not have to be direct. More specifically, indirect labeling using binding reactions such as antibodies against antibodies, or avidin to biotin, is also possible.

The concentration of AREG in a sample is determined based on the signal intensities measured for standard sample whose AREG concentration is already known.

The immobilized antibodies and the second antibodies used for the heterogeneous immunoassays mentioned above may be any antibodies as long as they recognize AREG, or fragments comprising the antigen-binding site thereof. Therefore, monoclonal antibodies, polyclonal antibodies, or a mixture or combination of both may be used. When both antibodies are monoclonal antibodies, combining monoclonal antibodies recognizing different epitopes is preferred.

Since the antigen to be measured is sandwiched by antibodies, such heterogenous immunoassays are called sandwich methods. As sandwich methods excel in measurement sensitivity and reproducibility, they are one of the preferred principles of measurement in the present invention.

The principles of competitive inhibition reactions can be applied to the heterogeneous immunoassays. More specifically, these are immunoassays based on the phenomenon that the insulin AREG in a sample competitively inhibits the binding between an antibody and the AREG of a known concentration. The AREG concentration in the sample can be determined by labeling the AREG of known concentration and measuring the amount of the AREG that reacted (or did not react) with the antibody.

A competitive reaction system is established by simultaneously reacting, with antibodies, antigens of a known concentration and antigens in a sample. Furthermore, analyses by an inhibitory reaction system are possible when antibodies are reacted with antigens of a known concentration after reacting with antigens in the sample. In both types of reaction systems, reaction systems that are superior in operability can be constructed by preparing either the antibodies or the antigens of known concentration (used as reagent components) as labeled components, and the other as the immobilized reagents.

The labeling components used in such heterogeneous immunoassays include radioisotopes, fluorescent substances, light-emitting substances, substances having enzymatic activity, macroscopically observable substances, and magnetically observable substances. Specific examples of these labeling substances are shown below.

Substances Having Enzymatic Activity:
peroxidase,
alkaline phosphatase,
urease, catalase,
glucose oxidase
lactate dehydrogenase,
or amylase, etc.

Fluorescent Substances:
fluorescein isothiocyanate,
tetramethylrhodamine isothiocyanate,
substituted rhodamine isothiocyanate,
dichlorotriazine isothiocyanate, etc.

Radioisotopes:
tritium,
$^{125}I$,
$^{181}I$, etc.

Of these, enzymes or such non-radioactive labels are among advantageous labels in terms of safety, operability, sensitivity, and such. Enzymatic labels can be linked to antibodies or to an AREG by known methods such as the periodate method, or maleimide method.

As the solid phase, beads, inner walls of a container, fine particles, porous carriers, magnetic particles, or such are used. Solids that have been fabricated using materials such as polystyrene, polycarbonate, polyvinyltoluene, polypropylene, polyethylene, polyvinyl chloride, nylon, polymethacrylate, latex, gelatin, agarose, glass, metal, ceramic, or such can be used for these solid phases. Solid materials to whose surface functional groups for chemically binding antibodies and such have been introduced are known. Known linking methods including chemical bonding such as poly-L-lysine or glutaraldehyde treatment, or physical adsorption can be applied for solid phases and antibodies (or antigens).

Although the steps of separating the solid phase from the liquid phase as well as washing steps are required in all heterogeneous immunoassays exemplified herein, these steps can easily be performed using immunochromatography, which is a variation of the sandwich method.

Specifically, the immobilized antibodies are fixed onto porous carriers capable of transporting sample solutions by capillary action. Then, a sample comprising AREG mixed with labeled antibodies is migrated through this by capillary action. During this migration, AREG reacts with the labeled antibodies, and then when it contacts the immobilized antibodies, it is trapped at that position. Labeled antibodies that have not reacted with AREG pass through without being trapped on the immobilized antibodies.

As a result, the presence of AREG can be detected by using as an indicator the signals of the labeled antibodies that remain at the position of the immobilized antibodies. If the labeled antibodies are preloaded upstream in the porous carrier, all reactions will be initiated and completed by simply instilling the sample solution, thus an extremely convenient reaction system can be constructed. In immunochromatography, labeled components that can be distinguished macroscopically, such as colored particles, can be combined to construct an analytical device that does not even need a special reader.

Furthermore, in immunochromatography, the sensitivity of AREG detection can be adjusted. For example, by adjusting the detection sensitivity to a value near an above cutoff value, the abovementioned labeled components will be detected when the cutoff value is exceeded. By using this kind of device, whether subjects are positive or negative can be determined very conveniently. A construct that enables the labels to be distinguished macroscopically can provide the necessary examination results when blood samples are simply applied to a device for immunochromatography.

Various methods are known as methods for adjusting detection sensitivity in immunochromatography. For example, a second immobilized antibody for adjusting detection sensitivity can be positioned between the position where samples are applied and the position of the immobilized antibodies (Japanese Patent Application Kokai Publication No. (JP-A) H06-341989 (unexamined, published Japanese patent application)). While the sample migrates from the position where it was applied to the position of the first immobilized antibody for label detection, AREG in the sample is trapped by the second immobilized antibody. After the second immobilized antibody is saturated, AREG can reach the position of the first immobilized antibody, which is downstream of the second antibody. As a result, AREG bound to the labeled antibody is detected at the position of the first immobilized antibody when the concentration of AREG included in the sample is above a certain concentration.

Next, homogeneous immunoassays will be described. In contrast to heterogeneous immunoassay methods that require separation of the reaction solution, as described above, AREG can also be measured by homogeneous analysis methods. Homogeneous analysis methods allow detection of antigen-antibody reaction products without separating them from the reaction solution.

A representative homogeneous analysis method is an immunoprecipitation reaction in which antigenic substances are quantitatively analyzed by examining precipitates produced in association with the antigen-antibody reaction. Polyclonal antibodies are generally used for the immunoprecipitation reactions. When applying monoclonal antibodies, multiple types of monoclonal antibodies that bind to different epitopes of AREG are preferably used. The products of precipitation reactions associated with the immunological reactions can be macroscopically observed, or they can be converted to numerical data by optical measurements.

Immunological particle agglutination reactions, which use as indicators the agglutination of antibody-sensitized fine particles by antigens, are common homogeneous analysis methods. As in the aforementioned immunoprecipitation reactions, polyclonal antibodies or a combination of multiple types of monoclonal antibodies can also be used in this method. Fine particles can be sensitized with antibodies through sensitization with a mixture of antibodies, or they can be prepared by mixing particles that have been separately sensitized with each type of antibody. Fine particles obtained in this manner give matrix-like reaction products upon contact with AREG. The reaction products can be detected as particle aggregates. Particle aggregation may be macroscopically observed, or may be converted into numerical data by optical measurements.

Immunoassay methods based on energy transfer and enzyme channeling are known as examples of homogeneous immunoassays. In methods utilizing energy transfer, different optical labels with donor/acceptor relationships are linked to each of a number of antibodies that recognize nearby epitopes on an antigen. When immunological reactions take place, they come closer to each other and energy transfer occurs, resulting in signals such as extinction or changes in fluorescence wavelength and the like. On the other hand, enzyme channeling uses a combination of enzymes, related in that the reaction product of one enzyme is the substrate of another, as labels for a number of antibodies bound to nearby epitopes. When they come close to each other due to immunological reactions, the enzyme reactions are enhanced, and therefore their binding can be detected as a change in enzyme reaction rates.

In the present invention, blood for measuring AREG can be prepared from blood drawn from patients. Preferred blood samples are serum or plasma. Serum or plasma samples can be diluted prior to taking measurements. Alternatively, whole blood can be measured as a sample, and the measured values can be corrected to determine the serum concentration. For example, concentration in whole blood can be corrected to concentration in serum by determining the percentage volume of blood cells in the same blood sample.

The methods of the present invention for treating lung cancers can treat various types of lung cancers that are responsive to erbB receptor inhibitors. Preferably, the lung cancers referred to in the present invention are non-small-cell lung cancers (NSCLC).

In the present invention, an erbB receptor inhibitor is administered to patients whose blood concentration of AREG has been determined to be lower than standard values. The erbB receptor inhibitor that is administered is determined according to general therapeutic protocols. Specifically, for an adult the daily dose is, for example, 10 to 2000 mg, ordinarily 20 to 1000 mg, specifically 50 to 700 mg, and more specifically 100 to 700 mg. For example, in a current standard therapeutic protocol for administering gefitinib, a daily dose of 250 mg is administered to an adult, regardless of gender or body weight.

In the present invention, erbB receptor inhibitors can be administered orally or parenterally. Examples of parenteral administration include intravenous injections.

Kits for treating lung cancers can be provided by combining elements used in the therapeutic methods of the present invention. More specifically, the present invention relates to kits for treating lung cancers, comprising the following elements:

(1) therapeutic agents for lung cancers comprising erbB receptor inhibitors as active ingredients; and (2) an instruction sheet stating that a patient whose blood AREG concentration is high compared to a standard value has low responsiveness to the therapeutic agents for lung cancers comprising an erbB receptor inhibitors as active ingredients.

The treatment kits of the present invention may also include the following element:

(3) an instruction sheet stating that a patient whose blood TGFA concentration is high compared to a standard value has low responsiveness to the therapeutic agents for lung cancers comprising erbB receptor inhibitors as active ingredients.

For example, therapeutic kits for lung cancers comprising the following elements (1) and (2) are included in the kits of the present invention for treating lung cancers:

(1) therapeutic agents for lung cancers comprising erbB receptor inhibitors as active ingredients; and (2) an instruction sheet stating that administration of erbB receptor inhibitors is not recommended for patients whose blood concentration of AREG or blood concentration of TGFA is higher than a standard value.

Alternatively, the kits of the present invention for treating lung cancers include kits for treating lung cancers that comprise the following elements (1) and (2):

(1) therapeutic agents for lung cancers which comprise erbB receptor inhibitors as active ingredients; and (2) an instruction sheet stating that erbB receptor inhibitors can be administered to patients whose blood concentration of AREG and blood concentration of TGFA both do not exceed standard values.

In addition to instructions relating to patients who should be receiving the administrations, the instruction sheets in the kits of the present invention for treating lung cancers may include a variety of information necessary for treatments using the above erbB receptor inhibitors. Specifically, information such as the mechanism of action of the pharmaceutical agents, anticipated side-effects, conditions for storing the pharmaceutical agents, date of manufacture of the pharmaceutical agents, or expiration date of the pharmaceutical agents may be included.

The methods of the present invention for treating lung cancers comprise administering the present pharmaceutical agents to patients who are responsive to erbB receptor inhibitors. To select patients who are responsive to erbB receptor inhibitors, a lung cancer patient's responsiveness to the pharmaceutical agents must be examined. Specifically, the present invention provides methods for examining responsiveness to agents for treating lung cancers that comprise erbB receptor inhibitors as active ingredients, in which the methods comprise the steps of:

(1) measuring AREG concentration in blood samples of lung cancer patients; and (2) determining that responsiveness of the patients to therapeutic agents for lung cancers that comprise erbB receptor inhibitors as active ingredients is low when the AREG concentration is high compared to a standard value.

The methods of the present invention for examining responsiveness to therapeutic agents for lung cancers can be carried out using the steps below. Specifically, the present invention provides methods for examining responsiveness to therapeutic agents for lung cancers that comprise erbB receptor inhibitors as active ingredients, in which the methods comprise the steps of:

(1) measuring AREG concentrations in blood samples of lung cancer patients;

(2) comparing the values measured in step (1) with measured values of blood AREG concentrations of patients who are responsive to erbB receptor inhibitors; and (3) indicating that the lung cancer patients are responsive to erbB receptor inhibitors, when the results of the comparison of step (2) show that the values measured in step (1) are at the same level as the values measured for patients confirmed to be responsive to erbB receptor inhibitors.

The examination methods of the present invention for responsiveness can also include the steps of:

(1) measuring TGFA concentrations in blood samples of lung cancer patients; and (2) judging that the patients have low responsiveness to the therapeutic agents for lung cancers comprising erbB receptor inhibitors as active ingredients when the AREG concentrations or TGFA concentrations or both are high compared to standard values.

As in the methods of evaluating the measured values of AREG, TGFA concentrations can be compared by the steps of:

(1) measuring TGFA concentrations in blood samples of lung cancer patients;

(2) comparing the values measured in step (1) with measured values of blood TGFA concentrations in patients who are responsive to erbB receptor inhibitors; and (3) indicating that the lung cancer patients are responsive to erbB receptor inhibitors when the results of the comparison of step (2) show that the values measured in step (1) are at the same level as the values measured for patients confirmed to be responsive to erbB receptor inhibitors.

In the methods of the present invention for examining responsiveness, blood AREG concentrations or blood TGFA concentrations can be measured by the above-described methods. The standard values or blood concentrations of patients who are responsive to erbB receptor inhibitors, which are to be compared with each of the measured values, can be set as described earlier.

The measured values for the blood concentrations of AREG or TGFA or both are evaluated, and when either one or both exceed standard values, the responsiveness of a subject to an erbB receptor inhibitor is shown to be low. In a preferred embodiment of the present invention, when the blood concentration of either AREG or TGFA exceeds a standard value, the responsiveness of a subject to an erbB receptor inhibitor is shown to be low. As already mentioned, in the examination methods of the present invention, values measured for patients confirmed to be responsive to erbB receptor inhibitors can be used as standard values.

Elements used to carry out the methods of the present invention for examining responsiveness to therapeutic agents for lung cancers comprising erbB receptor inhibitors as active ingredients can be combined in advance and provided as kits for examination. More specifically, the present invention provides kits for examining responsiveness to therapeutic agents for lung cancers comprising erbB receptor inhibitors as active ingredients, which comprise the following elements:

i. immunoassay reagents for measuring AREG blood concentration; and ii. a positive control for AREG The kits of the present invention can additionally comprise the following elements:

iii. immunoassay reagents for measuring TGFA blood concentration; and iv. a positive control for TGFA.

Immunoassay reagents that constitute the examination kits of the present invention may include reagents necessary for the various immunoassays described earlier. Specifically, reagents for immunoassays include antibodies that recognize the substances to be measured. The antibodies can be modified depending on the immunoassay format. ELISA can be used as a preferred assay format in the present invention. For example, ELISA generally uses a first antibody immobilized onto a solid phase, and a second antibody carrying a label.

That is, immunoassay reagents for ELISA may comprise a first antibody immobilized onto a solid phase carrier. As the solid phase carrier, fine particles or the inner walls of reaction containers may be used. Magnetic particles may be used as the fine particles. Multi-well plates such as 96-well microplates are often used as reaction containers. Containers for processing a large number of samples, which are equipped with a high density of wells of smaller volume than those of 96-well plates, are also known. In the present invention, the inner walls of these reaction containers can be used as solid phase carriers.

The immunoassay reagents for ELISA may further comprise a second antibody carrying a label. The second antibody for ELISA may be an antibody that is directly linked to an enzyme, or it may be indirectly linked with an enzyme. Methods for chemically linking enzymes to antibodies are well known. For example, immunoglobulins can be enzymatically cleaved to obtain fragments that carry a variable region. By reducing the —SS— bonds in such fragments to —SH groups, bifunctional linkers can be attached. By pre-linking the enzymes to the bifunctional linkers, the enzymes can be linked to the antibody fragments.

Alternatively, avidin-biotin binding or such may be used for indirectly linking an enzyme. That is, by contacting biotinylated antibodies with avidin-conjugated enzymes, the enzymes can be indirectly linked with the antibodies. In addition, enzymes can be indirectly linked with a second antibody by using a third antibody, which is an enzyme-labeled antibody that recognizes the second antibody. Enzymes such as those indicated above may be used as the enzymes for labeling antibodies, for example.

The kits of the present invention comprise a positive control for AREG A positive control for AREG comprises AREG whose concentration has been tested in advance. In the above methods of testing for responsiveness, for example, a preferred concentration can be used as the concentration set as a standard value. Alternatively, it is possible to combine a positive control having a higher concentration. The positive control for AREG in the present invention may additionally comprise TGFA of pre-tested concentration. A positive control comprising both AREG and TGFA is preferred as the positive control of the present invention.

Positive controls in the present invention are preferably in liquid form. In the present invention, blood samples are used as the samples. Therefore, the samples used as controls need to be in the form of liquids. Alternatively, by dissolving dried positive controls with given volumes of liquid at the time of use, controls yielding pre-tested concentrations may be prepared. If a volume of liquid necessary for dissolution is packaged together with a dried positive control, users will be able to obtain the necessary positive controls just by mixing these two. The AREG or TGFA for use as the positive control may be natural proteins or recombinant proteins. The kits of the present invention may additionally include not only a positive control but also a negative control. The positive or negative controls are used to verify that the results indicated by the immunoassays are correct.

Hereinbelow, the present invention will be specifically described with reference to Examples.

EXAMPLES

Patients

Between August 2002 and February 2005, 50 patients with progressive non-small-cell lung cancer for whom previous chemotherapy had shown no effects were treated with gefitinib (250 mg/day). Patients with locally advanced (stage IIIB) and metastasized (stage IV) cancers, and patients with postsurgically relapsed non-small-cell lung cancers who were resistant to one or more methods of conventional chemotherapy were enrolled in this experiment. The criteria for test subjects were the same as those described in the previous report (Kakiuchi S, et al. Hum. Mol. Genet. 2004; 13:3029-43). To give an overview, the subjects were patients who were at least 20 years old, had a performance status (PS) of 0, 1, or 2, and had no significant abnormalities in their liver or kidney function. Treatment was continued until the patient was dropped from the study due to disease progression, intolerable toxicity, withdrawal of consent to use the drug, or the like.

Serum was obtained one week before administration of gefitinib and stored at −80° C. The serum samples of 50 patients were used for ELISA analysis; of these, formalin-fixed primary non-small-cell lung cancer tissue samples were obtained from 13 of the patients treated with gefitinib for their recurrent and chemotherapy-resistance after they had undergone surgery as an initial treatment (nine adenocarcinoma patients, three squamous cell carcinoma patients, and one adenosquamous cell carcinoma patient).

The use of all clinical samples, which were obtained from patients with written consent, was approved by the Research Ethics Committee. Objective therapeutic effects on tumors at evaluable lesions were assessed every four weeks after the beginning of treatment, according to previously reported criteria (Kakiuchi S, et al. Hum. Mol. Genet. 2004; 13:3029-43). After four months of treatment, an overall evaluation of the treatment was carried out according to the following definitions:

Complete response (CR): patients judged to be CR at two treatments carried out with an interval of at least 28 days;

Partial Response (PR): patients judged to be PR or showing better effects at two treatments carried out with an interval of at least 28 days;

Stable Disease (SD): patients judged to be SD or showing better effects at two treatments carried out with an interval of least 28 days, but who were not CR or PR. SD is first assessed at a tumor assessment point 28 days or more after the start of gefitinib treatment; and Progressive Disease (PD): patients who were determined as PD at or before the first tumor assessment point, which is 28 days after the start of gefitinib treatment.

ELISA

Serum TGFA values were measured using commercially available ELISA kits (TGFA ELISA kit, R&D Systems, Minneapolis, Minn.) as described previously (Kakiuchi S, et al. Hum. Mol. Genet. 2004; 13:3029-43.; Ishikawa N, et al. Clin. Cancer Res. 2004; 10:8363-70). For detection of dissolved amphiregulin in serum, 96-well microtiter plates (Nalge Nunc International, Rochester, N.Y.) were coated with 1 ng/mL of primary antibody (anti-amphiregulin monoclonal antibody, R&D Systems) overnight. Each of the wells was then blocked with 300 μL PBS (pH 7.4) containing 1% BSA, 5% sucrose, and 0.05% $NaN_3$ for two hours, then serum samples diluted at a ratio of 1:3 in PBS (pH 7.4) containing 1% BSA were added to the wells, and this was left undisturbed. After washing with PBS (pH 7.4) containing 0.05% Tween 20, the wells were left to stand for two hours with 100 ng/mL of biotin-labeled anti-amphiregulin polyclonal antibody (R&D Systems), and then reacted with avidin-labeled peroxidase (DakoCytomation, Glostrup, Denmark) using a substrate reagent (R&D Systems).

The color reaction was stopped by adding 2 N sulfuric acid. Color intensity was determined using a photometer at 450 nm with a reference wavelength of 630 nm. A standard curve was drawn for each plate using recombinant amphiregulin or TGFA protein as a reference substance. Minimum detection limits for serum amphiregulin and TGFA were 10.1 pg/mL and 3.1 pg/mL, respectively. Western blot and immunoprecipitation assays using malignant pleural effusions, obtained from five patients with progressive non-small cell lung cancer in which serum amphiregulin/TGFA had been confirmed, were used to verify that these commercial anti-amphiregulin and anti-TGFA antibodies could specifically detect each of the proteins.

EGFR Mutations

Mutations at exons 18 to 21 of EGFR, which was reported as a hotspot of mutation (Lynch T J, et al. N. Engl. J. Med. 2004; 350:2129-39.; Paez J Q et al. Science 2004; 304:1497-500.; Pao W, et al. Proc. Natl. Acad. Sci. USA 2004; 101: 13306.11.; Tokumo M, et al. Clin. Cancer Res. 2005;

11:1167-73.; Mitsudomi T, et al. J. Clin. Oncol. 2005; 23:2513-20; from p-loop to activation loop, codon position 709-870), were screened in resected tumor tissues available from the thirteen non-small-cell lung cancer patients who were administered gefitinib (see above). Genomic DNAs were extracted by a previously reported method (Daigo Y, et al., Am. J. Pathol. 2001; 158:1623-31).

In summary, cancer tissues were immediately resuspended in 20 μL of buffer containing 10 mmol/L Tris-HCl (pH 8.3), 2.5 mmol/L $MgCl_2$, 50 mmol/L KCl, 0.45% NP40, 0.45% Tween 20, and 0.1 mg/mL proteinase K, and were left to stand overnight at 55° C. The mixture was boiled for ten minutes to inactivate the proteinase K, and was then used for PCR. Direct sequencing by PCR was carried out using the same primers for exons 18 to 21 as described elsewhere (Tokumo M, et al., Clin. Cancer Res. 2005; 11:1167-73).

Immunohistochemistry and Tissue Microarray

Samples used were 449 formalin-fixed primary cancer tissue samples (285 adenocarcinomas, 121 squamous cell carcinomas, 28 lung large-cell carcinomas, and 15 adenosquamous cell carcinomas) and adjacent normal lung tissue samples from patients who had undergone surgery. The histological patterns of the adenocarcinomas were divided into the following four subtypes:

acinar adenocarcinoma,
papillary adenocarcinoma,
bronchioloalveolar carcinoma, and
solid carcinoma with mucus formation.

Pathological stages were determined according to the classification of the Union Internationale Contre le Cancer (Travis W D, et al., 3rd ed. New York: Springer-Verlag; 1999).

Tumor tissue microarray analyses using these 449 formalin-fixed primary lung cancer tissues were carried out as previously published (Ishikawa N, et al., Clin. Cancer Res. 2004; 10:8363-70). To investigate the levels of amphiregulin and TGFA proteins in clinical samples with clinicopathologic diversity, the sections were stained using Envision+kit/horseradish peroxidase (HRP; DakoCytomation).

After blocking, the following antibodies were used to carry out this experiment: a 1:40 diluted rabbit anti-human amphiregulin antibody (Ab-1, Lab Vision Corp., Fremont, Calif.) and a 1:80 diluted mouse monoclonal anti-TGFA antibody (Ab-2, Oncogene Science, Manhasset, N.Y.). Each of the tissues was reacted with either HRP-labeled anti-rabbit or anti-mouse IgG as the secondary antibody. A chromogenic substrate was added and the specimens were counterstained with hematoxylin. Three independent physician-investigators individually assessed the presence of amphiregulin and TGFA semi-quantitatively, without prior knowledge of the clinical data. The intensity of cytoplasmic staining was scored using the following criteria: 0 (absent), 1+ (positive), and 2+ (strongly positive). The pattern of amphiregulin staining, which was cytoplasmic, nuclear, or both, was also determined as reported previously (Ebert M, et al., Cancer Res. 1994; 54:3959-62.; Bostwick D G, et al., Prostate 2004; 58:164-8).

Statistical Analysis

To compare patient characteristics and therapy effects, statistical analyses were performed using the StatView statistical program (SAS, Cary, N.C.). Associations between clinicopathologic diversity, including the presence of amphiregulin and/or TGFA in serum, and gefitinib responsiveness were compared using Fisher's tests. Tumor-specific survival rate and 95% confidence intervals (95% CI) were evaluated using the Kaplan-Meier method, and differences between the two groups were evaluated using log-rank tests. Risk factors associated with the prognosis were evaluated using a Cox proportional hazards regression model with a step-down procedure. As a result of the evaluation, proportional hazards assumptions were satisfied; that is, "only those variables with statistically significant univariate analysis results are also included in the multivariate analysis". The criterion for removing a variable was the likelihood ratio, which was based on the maximum partial likelihood (the non-match ratio to the model was P=0.05).

Example 1

Clinical Information

Fifty patients who satisfied certain conditions were each administered a daily dose of 250 mg of gefitinib. The median age of the patients was 62 years old (ranging from 30 to 80 years old); 36 patients were male and 14 were female (Table 3).

TABLE 3

A. Association between NSCLC patients' characteristics and response to gefitinib therapy

| Variables | Total n = 50 | PR + SD (disease-controlled cases) n = 20 (8 PR + 12 SD) | PD (progressive disease case) n = 30 | P value |
|---|---|---|---|---|
| Gender |
| Male | 36 | 12 | 24 | NS |
| Female | 14 | 8 | 6 | |
| Age in years |
| Median | | 60.5 | 62.0 | |
| Range | | 47-76 | 30-80 | |
| Histologic type |
| ADC | 40 | 15 | 25 | NS* |
| SCC | 7 | 4 | 3 | |
| ASC | 3 | 1 | 2 | |
| Disease stage |
| IIIB | 9 | 3 | 6 | NS** |
| IV | 28 | 9 | 19 | |
| Recurrence post surgery | 13 | 8 | 5 | |
| Bone metastasis |
| Yes | 18 | 9 | 9 | NS |
| No | 32 | 11 | 21 | |
| Brain metastasis |
| Yes | 17 | 6 | 11 | NS |
| No | 33 | 14 | 19 | |
| ECOG performance status |
| 0 | 14 | 7 | 7 | 0.037****+ |
| 1 | 26 | 12 | 14 | |
| 2 | 10 | 1 | 9 | |
| Number of prior chemotherapy |
| 1 | 29 | 13 | 16 | NS*** |
| 2 | 10 | 2 | 8 | |
| >2 | 11 | 5 | 6 | |
| Prior cisplatin or carboplatin administration |
| Yes | 34 | 13 | 21 | NS |
| No | 16 | 7 | 9 | |
| Smoking history |
| Never | 18 | 11 | 7 | 0.035***** |
| Former | 15 | 4 | 11 | |
| Current | 17 | 5 | 12 | |

TABLE 3-continued

Serum AREG

| | | | | |
|---|---|---|---|---|
| Positive | 14 | 2 | 12 | 0.026+ |
| Negative | 36 | 18 | 18 | |

Serum TGFA

| | | | | |
|---|---|---|---|---|
| Positive | 15 | 2 | 13 | 0.014+ |
| Negative | 35 | 18 | 17 | |

Serum AREG or TGFA

| | | | | |
|---|---|---|---|---|
| Positive | 22 | 3 | 19 | 0.001+ |
| Negative | 28 | 17 | 11 | |

B. Cox's proportional hazards model analysis of prognostic factors in patients with progressive NSCLC who were treated with gefitinib

| Variables | Hazard ratio (95% CI) | P value |
|---|---|---|
| Univariate analysis | | |
| AREG (+/−) | 2.235 (1.050-4.761) | 0.037+ |
| TGFA (+/−) | 3.315 (1.557-7.059) | 0.002+ |
| AREG or TGFA (+/−) | 2.510 (1.197-5.262) | 0.018+ |
| Age (65≧/<65) | 1.044 (0.487-2.237) | 0.912 |
| Gender (male/female) | 1.555 (0.885-3.532) | 0.291 |
| Histologic type (others/ADC+) | 1.613 (0.848-4.013) | 0.309 |
| Disease Stage (IIIB/others) | 1.088 (0.445-2.706) | 0.8390 |
| Performance status (2/0-1) | 6.707 (2.544-17.682) | 0.001* |
| Smoking history (smoker/never smoked) | 1.596 (0.736-3.462) | 0.237 |
| Multivariate analysis | | |
| AREG (+/−) | 1.042 (0.384-2.825) | 0.835 |
| TGFA (+/−) | 2.457 (1.072-5.625) | 0.034+ |
| Performance status (2/0-1) | 4.792 (1.420-16.171) | 0.012+ |

Abbreviations: ADC, adenocarcinoma; SCC, squamous cell carcinoma; ASC, adenosquamous cell carcinoma; NS, not significant.
*Adenocarcinoma (ADC) versus others (SCC, squamous-cell carcinoma; and ASC, adenosquamous cell carcinoma).
**IIIB versus other classifications.
***PS 0-1 versus PS 2.
****Previous chemotherapy 0-1 versus other therapies.
*****Never smoked versus others.
+P < 0.05 (Fisher's test).
NS: no significant difference + ADC adenocarcinoma.
P < 0.05

Performance status (PS) according to the Eastern Cooperative Oncology Group (ECOG) was 0 for 14 patients, 1 for 26 patients, and 2 for ten patients. Twenty-one patients had been treated with at least two lines of chemotherapy, and 34 had received chemotherapy using a platinum formulation. At the start of the study, 32 patients were current (17) or former (15) smokers. In terms of histological diagnosis, 40 people (80.0%) had adenocarcinomas, seven (14.0%) had squamous cell carcinomas, and three (6.0%) had adenosquamous cell carcinomas.

After gefitinib therapy, eight patients were classified as PR and none as CR; 12 patients were classified as SD, and 30 as PD. The tumor response rate (CR+PR/CR+PR+SD+PD) for gefitinib therapy was 16.0%, and the disease control rate (CR+PR+SD/CR+PR+SD+PD) was 40.0%. Final judgment was made in July 2005, more than four months after the last patient was enrolled in the therapy. The median follow-up time was 240 days (the range was 33-1011 days).

Example 2

Serum Amphiregulin/Transforming Growth Factor-α Concentrations, Clinicopathologic Characteristics, and Responsiveness to Gefitinib Therapy As a result of examining genes expressed in tumors of progressive non-small-cell lung cancer patients who had been treated with second-line to seventh-line gefitinib monotherapy by cDNA microarray analysis, amphiregulin and TGFA were found to be significantly overexpressed in PD cases, but hardly expressed in PR cases (P values in the permutation tests were $9.3 \times 10^{-12}$ and 0.0095, respectively; Kakiuchi S, et al., Hum. Mol. Genet. 2004; 13:3029-43).

Figure 2:
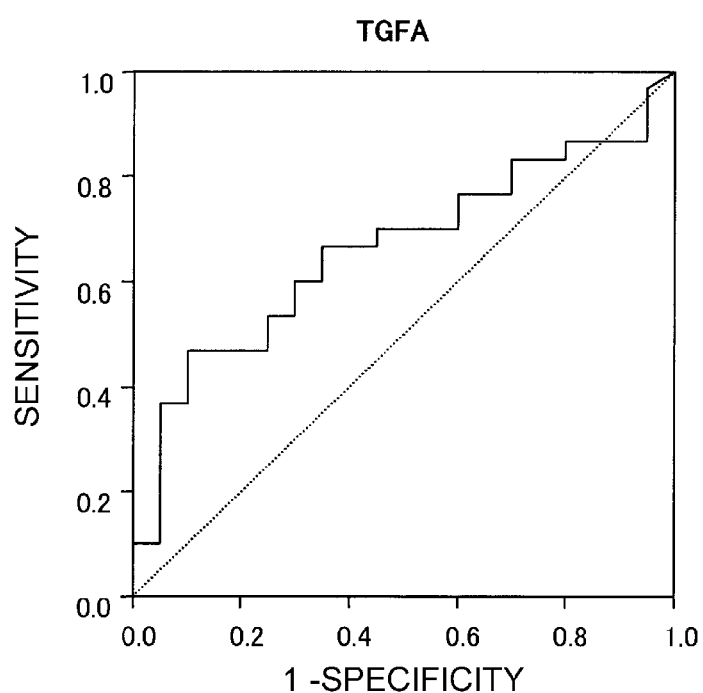
FIG. 2 shows ROC curves indicating the sensitivities and false-positive ratios obtained when using various cutoff values for serum amphiregulin concentration (A) or serum TGFA concentration (B) to predicatively diagnose tumor-reducing effects in 50 patients treated with gefitinib therapy.
Figure 2:
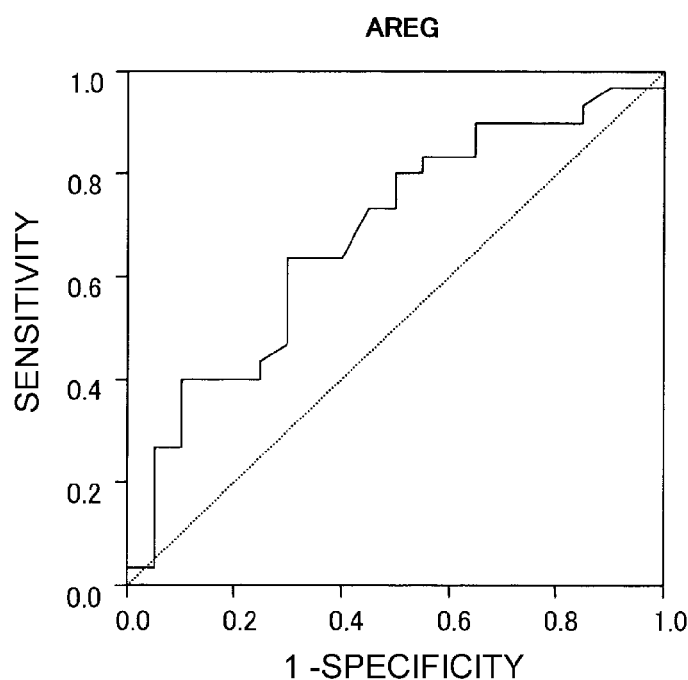

To establish a routine and less invasive clinical testing method for predicting responsiveness to a drug, two proteins were used as serological markers. More specifically, ELISA was carried out for both proteins using serum samples collected from 50 different non-small-cell lung cancer patients treated with gefitinib. "Positive" or "negative" judgements were made based on cutoff values for each of the proteins (93.8 pg/mL for amphiregulin and 15.6 pg/mL for TGFA). The cutoff values were set by producing ROC curves according to optimal diagnostic accuracy and likelihood ratios for distinguishing PD cases from disease-controlled cases (PR+SD) (FIG. 2). According to these cutoff values, of the 50 serum samples, serum from 14 patients (28.0%) was judged as positive for amphiregulin, and serum of 15 patients (30.0%) was positive for TGFA (FIG. 1).

As shown in Table 1, the association between serum amphiregulin, TGFA positivity, and gefitinib therapy was analyzed in this group of patients. Of the 30 PD patients, 12 (40.0%) serum samples were positive for amphiregulin, whereas 18 out of 20 (90.0%) samples collected from disease-controlled (PR or SD) patients were negative (P=0.026 according to the Fisher's test). Thirteen out of 30 (43.3%) samples obtained from PD patients were positive for TGFA, whereas 18 out of 20 (90.0%) samples from PR or SD patients were negative (P=0.014 according to the Fisher's test). At least one protein was positive in 19 out of 30 (63.3%) serum samples collected from PD patients, whereas 17 out of 20 (85.0%) samples from PR+SD patients were negative (P=0.001 according to the Fisher's test). This indicates that combined analysis using both amphiregulin and TGFA should be a good predictive marker of poor response in 63% of PD cases. The false-positive rate for indicating PD was only 15.0%.

Table 1 also shows the association between clinicopathologic factors and the responsiveness to gefitinib therapy of the 50 patients. In this study, both performance status (0/1 versus 2; P=0.037 according to the Fisher's test) and smoking history (current and former smokers versus those who had never-smoked; P=0.035 according to the Fisher's test) as well as amphiregulin and/or TGFA positivity were similarly found to be significantly associated with responsiveness to gefitinib. As mentioned above, 12 out of 14 patients who were amphiregulin-positive, as well as 13 out of 15 patients who were TGFA-positive, revealed no benefit from gefitinib therapy. 19 of the 22 patients with positive values for either one of the markers were judged to be PD.

Figure 3:
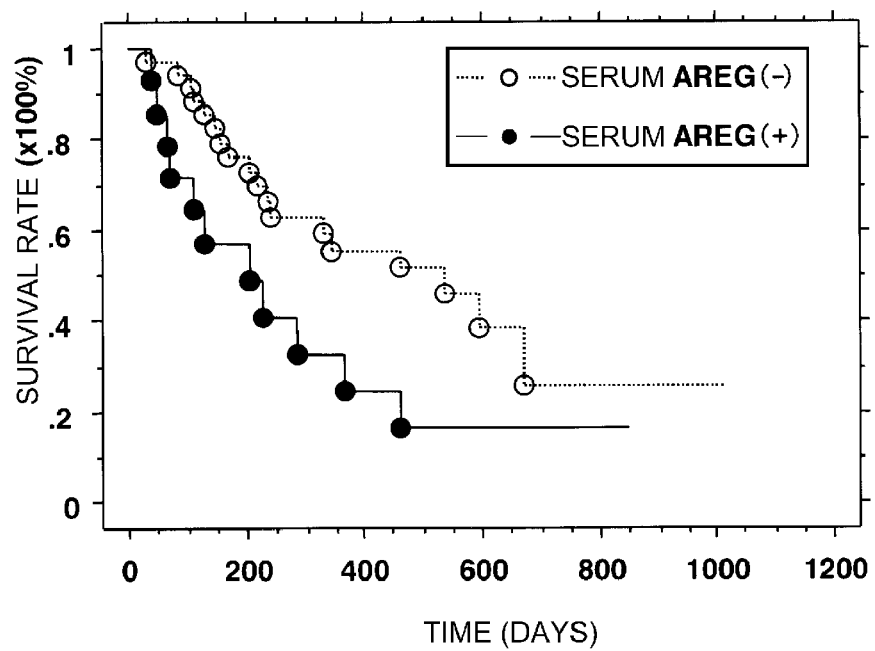
FIG. 3 shows the results of Kaplan-Meier analysis of the tumor-specific survival rate of 50 gefitinib-treated patients, according to positive or negative concentrations of serum amphiregulin (A) or serum TGFA (B). Differences between these groups were evaluated using a log-rank test.
Figure 3:
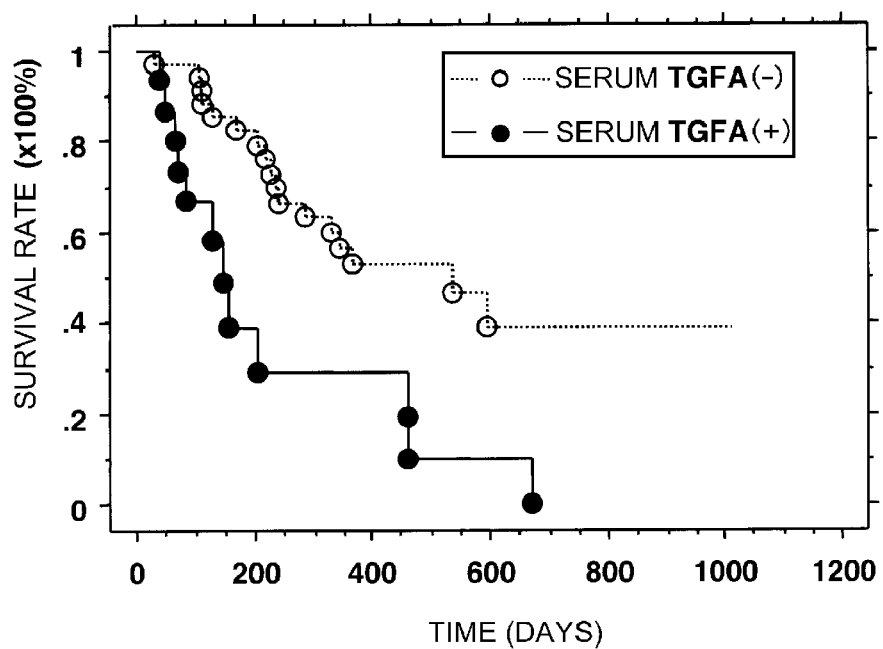

The median survival time of amphiregulin-negative patients treated with gefitinib was significantly longer than that of amphiregulin-positive patients (P=0.032 according to the log-rank test; FIG. 3A). The same result was observed in TGFA-negative patients (P=0.001 according to the log-rank test; FIG. 3B). Univariate analysis was also used to evaluate associations between patient prognosis and other factors, including age, gender (male versus female), PS (0/1 versus 2), disease stage (IIIB versus other stages), smoking history (current or former smoker versus those who had never-smoked), histologic classification (adenocarcinoma versus other histologic types), serum amphiregulin levels (positive versus negative), and serum TGFA levels (positive versus negative) (Table 4).

TABLE 4

Cox's proportional hazards model analysis of prognostic factors in patients with progressive NSCLC who were treated with gefitinib

| Variables | Hazard ratio (95% CI) | P value |
|---|---|---|
| Univariate analysis | | |
| Amphiregulin (+/−) | 2.235 (1.050-4.761) | 0.037* |
| TGF-α (+/−) | 3.315 (1.557-7.059) | 0.002* |
| Amphiregulin or TGF-α (+/−) | 2.510 (1.197-5.262) | 0.016* |
| Age ($\geq$65/<65 y) | 1.044 (0.487-2.237) | 0.912 |
| Gender (male/female) | 1.555 (0.685-3.532) | 0.291 |
| Histologic type (others/ADC) | 1.613 (0.648-4.013) | 0.309 |
| Disease Stage (IIIB/others) | 1.098 (0.445-2.706) | 0.8390 |
| PS (2/0-1) | 6.707 (2.544-17.682) | <0.001* |
| Smoking history (smoker/never smoked) | 1.596 (0.736-3.462) | 0.237 |
| Multivariate analysis | | |
| Amphiregulin (+/−) | 1.042 (0.384-2.825) | 0.935 |
| TGF-α (+/−) | 2.457 (1.072-5.625) | 0.034* |
| PS (2/0-1) | 4.792 (1.420-18.171) | 0.012* |

*P < 0.05

Of these variables, serum amphiregulin positivity [odds ratio (OR), 2.235; 95% CI, 1.050-4.761; P=0.037], serum TGFA positivity (OR, 3.315; 95% CI, 1.557-7.059; P=0.002), and PS (OR, 6.707; 95% CI, 2.544-17.682; P<0.002) were significantly associated with a poor prognosis. However, the results of multivariate analysis revealed that serum TGFA levels (OR, 2.457; 95% CI, 1.072-5.625; P=0.034) and PS (OR, 4.792; 95% CI, 1.420-16.171; P=0.012) are not significantly associated with prognostic signs for progressive non-small-cell lung cancer patients who received gefitinib therapy.

To examine whether there is a mechanistic relationship between EGFR mutations and the levels of serum amphiregulin and TGFA, direct sequencing of the EGFR tyrosine kinase domain (exons 18-21) by PCR was carried out using tumors from 13 patients whose sera were also analyzed by ELISA. As shown in Table 5, EGFR mutations were detected in four out of eight (50%) patients showing the PR or SD condition after gefitinib treatment and in two out of five (40%) patients showing the PD condition, indicating that there was no significant association between EGFR mutations and the levels of serum amphiregulin and TGFA.

TABLE 5

Clinicopathologic characteristics and EGFR mutation status of NSCLC patients

| Case | Age, y | Gender | Smoking history | Histologic type | ECOG Performance Status | Serum AREG | Serum TGFA | EGFR mutation | Response to gefitinib |
|---|---|---|---|---|---|---|---|---|---|
| 1 | 69 | Female | Never | ADC | 1 | Negative | Negative | deletion of E746-A750 | PR |
| 2 | 66 | Female | Never | ADC | 1 | Negative | Negative | deletion of E746-A750 | PR |
| 3 | 57 | Male | Never | ADC | 1 | Negative | Negative | L858R | PR |
| 4 | 64 | Male | Former | SCC | 1 | Negative | Positive | ND | PR |
| 5 | 64 | Female | Never | SCC | 0 | Negative | Negative | L858R | SD |
| 6 | 53 | Male | Current | ASC | 1 | Negative | Negative | ND | SD |
| 7 | 47 | Male | Former | ADC | 0 | Negative | Negative | ND | SD |
| 8 | 48 | Female | Never | ADC | 1 | Negative | Negative | ND | SD |
| 9 | 46 | Male | Current | ADC | 0 | Negative | Negative | L858R | PD |
| 10 | 53 | Male | Former | ADC | 1 | Negative | Positive | L858R | PD |
| 11 | 59 | Male | Former | ADC | 2 | Positive | Negative | ND | PD |
| 12 | 80 | Male | Never | SCC | 2 | Positive | Positive | ND | PD |
| 13 | 69 | Female | Never | ADC | 0 | Negative | Negative | ND | PD |

PR, partial response;
SD, stable;
PD, progressive
ND, no mutation was detected

Example 3

Expression Status of Amphiregulin and Transforming Growth Factor-α in Lung Cancer Tissues Obtained by Random Sampling In order to examine the clinical significance of amphiregulin and TGFA overexpression, the expression of amphiregulin and TGFA proteins was also examined by means of tissue microarrays using tissues collected from 449 non-small-cell lung cancer patients who had undergone surgery, selected by random sampling. As reported previously, amphiregulin was mainly detected at the cytoplasm and/or nucleus of tumor cells (Ebert M, et al., Cancer Res. 1994; 54:3959-62.; Bostwick D G, et al., Prostate 2004; 58:164-8). TGFA was mainly stained at the cytoplasm of tumor cells.

As shown in Table 6, gender (higher in males; P<0.001 according to the Fisher's test), histological classification (higher in nonadenocarcinomas; P<0.001 according to the Fisher's test), and smoking history (higher in current and former smokers; P<0.001 according to the Fisher's test) were significantly associated with amphiregulin positivity. A similar tendency was observed with TGFA (higher in males, P=0.001; higher in nonadenocarcinomas, P<0.001; and higher in current and former smokers, P=0.005 according to the Fisher's test). The amphiregulin positivity was significantly higher in nonbronchioloalveolar (P=0.004) and nonpapillary (P=0.011) types of adenocarcinoma, but a significant difference was not observed for TGFA positivity.

TABLE 7

Cox's proportional hazards model analysis of prognostic factors in patients with progressive NSCLC who were not treated with gefitinib

| Variables | Hazard ratio (95% CI) | P values |
|---|---|---|
| Univariate analysis | | |
| AREG (+/−) | 1.420 (1.075-1.880) | 0.013[+] |
| TGFA (+/−) | 1.403 (1.034-1.908) | 0.029[+] |
| Age (65≧/<65) | 1.474 (1.115-1.949) | 0.006[+] |

TABLE 6

Association between AREG/TGFA positivity in NSCLC tissues and clinical characteristics

| | | AREG status | | | TGFA status | | |
|---|---|---|---|---|---|---|---|
| Variables | Total n = 449 | AREG-positive n = 163 | AREG-negative n = 286 | P value | TGFA-positive n = 301 | TGFA-negative n = 148 | P value |
| Gender | | | | | | | |
| Male | 310 | 134 | 176 | <0.001[+] | 223 | 87 | 0.001[+] |
| Female | 139 | 29 | 110 | | 78 | 61 | |
| Age, y | | | | | | | |
| <65 | 215 | 77 | 148 | NS | 144 | 71 | NS |
| ≧65 | 234 | 86 | 138 | | 157 | 77 | |
| Histologic type | | | | | | | |
| ADC | 285 | 78 | 207 | <0.001*[+] | 170 | 115 | <0.001*[+] |
| SCC | 121 | 61 | 60 | | 94 | 27 | |
| LCC | 28 | 19 | 9 | | 26 | 2 | |
| ASC | 15 | 5 | 10 | | 11 | 4 | |
| Dominant histologic subtype (n = 273) | | | | | | | |
| Papillary | 218 | 52 | 166 | 0.011[+] | 127 | 91 | NS |
| Nonpapillary | 55 | 23 | 32 | | 32 | 23 | |
| BAC | 138 | 27 | 111 | 0.004* | 78 | 60 | NS |
| Non-BAC | 135 | 48 | 87 | | 81 | 54 | |
| Disease stage | | | | | | | |
| I + II + IIIA | 359 | 130 | 229 | NS | 248 | 111 | NS |
| IIIB | 90 | 33 | 57 | | 53 | 37 | |
| T | | | | | | | |
| T1 + T2 | 320 | 108 | 212 | NS | 217 | 103 | NS |
| T3 + T4 | 129 | 55 | 74 | | 84 | 45 | |
| N | | | | | | | |
| N0 + N1 | 336 | 114 | 222 | NS | 221 | 115 | NS |
| N2 + N3 | 113 | 49 | 64 | | 80 | 33 | |
| Smoking history | | | | | | | |
| Never-smoked | 139 | 25 | 114 | <0.001* | 80 | 59 | 0.005* |
| Smoker | 310 | 138 | 172 | | 221 | 89 | |

(n = 449)
Abbreviations: LCC, large-cell carcinoma; and BAC, bronchioloalveolar carcinoma.
[+]P < 0.05 (Fisher's test).
*ADC versus other classifications.

The median survival time of amphiregulin-negative patients was significantly longer than that of amphiregulin-positive patients (P=0.013 according to the log-rank test; Table 7). Similarly, the median survival time of the TGFA-negative patients was longer than that of positive patients (P=0.029 according to the log-rank test; Table 7).

TABLE 7-continued

Cox's proportional hazards model analysis of prognostic factors in patients with progressive NSCLC who were not treated with gefitinib

| Variables | Hazard ratio (95% CI) | P values |
|---|---|---|
| Gender (male/female) | 1.600 (1.164-2.193) | 0.004[+] |
| Histologic type (others/ADC) | 1.401 (1.063-1.848) | 0.017[+] |

TABLE 7-continued

Cox's proportional hazards model analysis of prognostic factors in patients with progressive NSCLC who were not treated with gefitinib

| Variables | Hazard ratio (95% CI) | P values |
|---|---|---|
| T factor (T3 + T4/T1 + T2) | 1.931 (1.451-2.571) | <0.001+ |
| N factor (N2 + N3/N0 + N1) | 2.882 (2.174-2.882) | <0.001+ |
| Multivariate analysis | | |
| AREG (+/−) | 1.078 (0.797-1.456) | 0.627 |
| TGFA (+/−) | 1.280 (0.929-1.764) | 0.130 |
| Age (65≧/<65) | 1.943 (1.456-2.593) | <0.001+ |
| Gender (male/female) | 1.587 (1.120-2.252) | 0.010+ |
| Histologic type (others/ADC) | 1.133 (0.831-1.543) | 0.431 |
| T factor (T3 + T4/T1 + T2) | 1.695 (1.261-2.278) | 0.063 |
| N factor (N2 + N3/N0 + N1) | 3.174 (2.353-4.274) | <0.001+ |

+P < 0.05

Gefitinib was developed as a "selective" inhibitor of EGFR tyrosine kinase. However, no clear association between EGFR levels and the responsiveness of cancer cells to gefitinib has been found in in vitro or in vivo systems. Multivariate analysis of patients in previous studies suggested that the response rate to gefitinib in females are higher than in males and higher in patients with adenocarcinomas than in patients with squamous cell carcinomas (Fukuoka M et al., J. Clin. Oncol. 2003; 21:2237-46.; Kim Y H et al., Clin. Cancer Res. 2004; 10:7311-7).

Recent clinical studies have suggested that patients for whom gefitinib is expected to be efficacious have bronchioloalveolar or dominant papillary types of adenocarcinoma and have no history of smoking (the above-mentioned Kim Y H et al. 2004; Miller V A et al., J. Clin. Oncol. 2004; 22:1103-9). Recently, studies by Lynch et al. (Lynch T J., et al., N. Engl. J. Med. 2004; 350:2129-39) and Paez et al. (Paez J G et al., Science 2004; 304:1497-500) showed that mutations in the tyrosine kinase domain of EGFR were associated with the sensitivity of non-small-cell lung cancers to gefitinib. Clinicopathologic determinants of gefitinib sensitivity, including EGFR mutations, are predictive to a certain extent; however, none of the known factors can perfectly predict the responsiveness of non-small-cell lung cancers to gefitinib (the above-mentioned Lynch T J., et al., 2004; the above-mentioned Paez J G et al., 2004; Pao W et al., Proc. Natl. Acad. Sci. USA 2004; 101:13306-11.; Tokumo M et al., Clin. Cancer Res. 2005; 11:1167-73.; Mitsudomi T et al., J. Clin. Oncol. 2005; 23:2513-20.; the above-mentioned Kakiuchi S et al., 2004).

Moreover, the clinical benefits of gefitinib treatment are not restricted to objective responses, such as PR, and should be applied to SD patients as well (the above-mentioned Kakiuchi S et al., 2004). In previously reported clinical trials (the above-mentioned Fukuoka M et al., 2003; Kim Y H et al., 2004), one group of patients showed an improvement in symptoms and prolonged stabilization of disease without any measurable reduction in tumor size. This study agrees with the studies of the present invention: that is, the survival time of PR+SD group patients was significantly prolonged compared to that of PD patients (P=0.011 according to the log-rank test).

Analyses of mutations or expression profiles are time-consuming procedures and require biopsy samples containing a sufficient number of cancer cells. Patients with progressive non-small-cell lung cancer are rarely candidates for surgical operation, and further their pathologic diagnosis does not always require invasive biopsy sample collection of tissues for selection of their treatment protocols. Thus, the above procedures such as analyses of mutations or expression profiles are not appropriate for routine diagnosis of drug responsiveness. In fact, the incidence of major complications related to transbronchial biopsy is 0.5% to 6.8% (British Thoracic Society. Guidelines on diagnostic flexible bronchoscopy. Subcommittee on Standards of Care Committee, British Thoracic Society. Thorax 2001; 56:i1-21). Therefore, the present inventors considered it necessary to urgently establish a safe and less invasive system for predicting the responsiveness of individual patients to pharmaceutical agents, such as a serologic test, which could be used easily at any hospital.

The present inventors discovered that amphiregulin and TGFA, both ligands for EGFR and ErbBs, were significantly overexpressed in tumor cells not responsive to gefitinib, but hardly detectable in responsive cells (the above-mentioned Kakiuchi S et al., 2004). Examination of amphiregulin and TGFA serum values in a group of patients with progressive non-small-cell lung cancer revealed that amphiregulin and TGFA proteins may have a high diagnostic value for predicting a poor response to gefitinib in such patients. Twelve of the 30 (40.0%) patients who were not responsive to gefitinib were positive for serum amphiregulin, and 13 of the 30 (43.3%) were positive for serum TGFA. Combining these two markers increased the sensitivity of detection of nonresponsive patients to 63.3%.

Known methods for analyzing EGFR mutations enable the selection of PR patients, but can hardly recognize SD patients at all (the above-mentioned Lynch T J., et al., 2004; Paez J G et al., 2004; Pao W et al., 2004; Tokumo M et al., 2005; Mitsudomi T et al., 2005). On the other hand, based on the present invention, prediction systems using these two markers can distinguish PD cases from PR or SD patients, chiefly for gefitinib. This is one of the important advantages of the present invention. In fact, statistical analysis also supports the hypothesis that the levels of serum amphiregulin and TGFA are biologically unrelated to EGFR mutation status.

This study also showed that the survival time of amphiregulin or TGFA-positive patients is short compared to that of negative patients. In particular, diagnosis using these serological markers showed that each of the markers is independently related to a poor prognosis. An initial analysis of the primary end point of a phase III trial (Iressa survival rate evaluation in 1,692 lung cancer patient cases; http://www.astrazeneca.com/pressrelease/4245.aspx) revealed that in a double-blind study, gefitinib could not always prolong survival time as compared to a placebo in all parent populations (hazard ratio, 0.89; P=0.11; median, 5.6 versus 5.1 months) and adenocarcinoma patients (hazard ratio, 0.83; P=0.07; median, 6.3 versus 5.4 months). This was despite statistically significant improvements in the objective response rate in these populations, and survival benefits for patients of Oriental origin or patients who had never smoked.

Results obtained by the present inventors suggest that serum amphiregulin and/or TGFA levels could be useful in selecting patients who are likely to respond poorly to gefitinib and who would receive hardly any life-prolonging benefit from it, while extending the benefit of gefitinib to a larger population of patients who should in fact receive benefits from this treatment. At present, detecting serum amphiregulin and TGFA is the only routine and meaningful method for predicting non-responsiveness of progressive non-small-cell lung cancers to gefitinib treatment. Therefore, it will be useful in developing diagnostic kits based on the present invention to examine serum amphiregulin and TGFA positivities upon selecting gefitinib therapy.

The importance of the EGFR ligand autocrine pathway in growth and survival of lung cancer cells is indisputable (Fontanini G et al., Clin. Cancer Res. 1998; 4:241-9.; Hurbin A et al., J. Biol. Chem. 2002; 277: 49127-33). However, the role of amphiregulin and TGFA in the development and growth of lung cancer cells is not well understood, although several lines of evidence suggest that overexpression of amphiregulin is associated with a shortened survival time for patients with non-small-cell lung cancer (the above-mentioned Fontanini G et al., 1998). Studies by the present inventors also revealed that amphiregulin and TGFA proteins in non-small-cell lung cancer tissues are likely to correlate to a certain extent with a poor prognosis for patients who have undergone surgical operation. In addition, being male, having nonadenocarcinoma, and having a history of smoking were associated with amphiregulin and TGFA positivity in non-small-cell lung cancer tissues, and some histologic types of adenocarcinoma (nonpapillary and nonbronchioloalveolar types) were also associated with amphiregulin positivity.

Recently, other research groups have reported that gefitinib was particularly effective in dominant papillary and/or bronchioloalveolar type adenocarcinomas; their data also suggested that amphiregulin/TGFA expression and histological classification are associated with gefitinib resistance. On the other hand, the anti-apoptotic activity of amphiregulin in human lung adenocarcinoma cells was recently reported (the above-mentioned Hurbin A et al., 2002). To investigate whether the anti-apoptotic activity of amphiregulin induces gefitinib resistance in non-small-cell lung cancers, a biological analysis using a gefitinib-sensitive but amphiregulin-non-expressing non-small-cell lung cancer cell line, PC-9, was carried out in advance. As a result, the antitumor activity of gefitinib on PC-9 cells was found to be dramatically reduced upon autocrine secretion of amphiregulin (the above-mentioned Kakiuchi S et al., 2004). This result strongly suggests that although growth factor signaling by EGFR is associated with various steps due to the multiplicity of ligands, dimerization factors, effectors, downstream pathways, and such, amphiregulin is a principal activator of the ligand-receptor autocrine pathway and induces resistance of cancer cells to gefitinib.

In conclusion, the present invention showed that serum amphiregulin and TGFA values are the most important factors in predicting the responsiveness of non-small-cell lung cancers to gefitinib. Measurement of serum amphiregulin and TGFA values is a routinely feasible, non-invasive, and inexpensive method for predicting responsiveness to the erbB receptor inhibitor.

INDUSTRIAL APPLICABILITY

The present invention is useful for predicting the therapeutic benefits of erbB receptor inhibitors against lung cancers. Gefinitib (product name: Iressa®) and such are included among the erbB receptor inhibitors. Furthermore, the present invention provides methods for treating lung cancers using erbB receptor inhibitors. Patients predicted to have low responsiveness to erbB receptor inhibitors can be identified according to the present invention. More specifically, the present invention enables the more sensitive detection of patients who could not be expected to show responsiveness to erbB receptor inhibitors. That is, the present invention enables patients who are responsive to erbB receptor inhibitors to be detected with greater specificity. As a result, according to the present invention, more effective lung cancer therapies can be carried out using erbB receptor inhibitors.

The invention claimed is:

1. A method for examining the responsiveness to a therapeutic agent for a lung cancer comprising an erbB receptor inhibitor as an active ingredient, wherein the method comprises the steps of:
   (1) measuring amphiregulin (AREG) concentration in a blood sample of a lung cancer patient; and
   (2) determining that responsiveness of the patient to a therapeutic agent for a lung cancer comprising an erbB receptor inhibitor as an active ingredient is low, when the AREG concentration is high compared to a standard value.

2. The examination method of claim 1, which additionally comprises the steps of
   (1) measuring the transforming growthfactor-alpha (TGFA) concentration in a blood sample of a lung cancer patient; and
   (2) determining that responsiveness of the patient to a therapeutic agent for a lung cancer comprising an erbB receptor inhibitor as an active agent is low, when the AREG concentration or the TGFA concentration or both are higher than standard values.

3. The method of claim 1, wherein the responsiveness of the patient to a therapeutic agent for a lung cancer comprising an erbB receptor inhibitor as an active agent is determined to be low, when the AREG concentration or TGFA concentration is high compared to a standard value.

4. The examination method of claim 1, which comprises measuring the AREG concentration of a blood sample using an immunoassay.

* * * * *

SEQUENCE LISTING

```
<160> NUMBER OF SEQ ID NOS: 2

<210> SEQ ID NO 1
<211> LENGTH: 1274
<212> TYPE: DNA
<213> ORGANISM: Homo sapiens
<220> FEATURE:
<221> NAME/KEY: CDS
<222> LOCATION: (215)..(973)

<400> SEQUENCE: 1
ggggagacgt tcgcacacct gggtgccagc gccccagagg tcccgggaca gcccgaggcg        60
ccgcgcccgc cgcccccgagc tccccaagcc ttcgagagcg gcgcacactc ccggtctcca      120
ctcgctcttc caacacccgc tcgttttggc ggcagctcgt gtcccagaga ccgagttgcc      180
ccagagaccg agacgccgcc gctgcgaagg acca atg aga gcc ccg ctg cta ccg     235
                                      Met Arg Ala Pro Leu Leu Pro
                                        1               5 ccg gcg ccg gtg gtg ctg tcg ctc ttg ata ctc ggc tca ggc cat tat        283
Pro Ala Pro Val Val Leu Ser Leu Leu Ile Leu Gly Ser Gly His Tyr
         10                  15                  20 gct gct gga ttg gac ctc aat gac acc tac tct ggg aag cgt gaa cca        331
Ala Ala Gly Leu Asp Leu Asn Asp Thr Tyr Ser Gly Lys Arg Glu Pro
    25                  30                  35 ttt tct ggg gac cac agt gct gat gga ttt gag gtt acc tca aga agt        379
Phe Ser Gly Asp His Ser Ala Asp Gly Phe Glu Val Thr Ser Arg Ser
40                  45                  50                  55 gag atg tct tca ggg agt gag att tcc cct gtg agt gaa atg cct tct        427
Glu Met Ser Ser Gly Ser Glu Ile Ser Pro Val Ser Glu Met Pro Ser
```

```
                60                    65                    70
agt agt gaa ccg tcc tcg gga gcc gac tat gac tac tca gaa gag tat         475
Ser Ser Glu Pro Ser Ser Gly Ala Asp Tyr Asp Tyr Ser Glu Glu Tyr
         75                    80                    85 gat aac gaa cca caa ata cct ggc tat att gtc gat gat tca gtc aga         523
Asp Asn Glu Pro Gln Ile Pro Gly Tyr Ile Val Asp Asp Ser Val Arg
         90                    95                   100 gtt gaa cag gta gtt aag ccc ccc caa aac aag acg gaa agt gaa aat         571
Val Glu Gln Val Val Lys Pro Pro Gln Asn Lys Thr Glu Ser Glu Asn
        105                   110                   115 act tca gat aaa ccc aaa aga aag aaa aag gga ggc aaa aat gga aaa         619
Thr Ser Asp Lys Pro Lys Arg Lys Lys Lys Gly Gly Lys Asn Gly Lys
120                   125                   130                   135 aat aga aga aac aga aag aag aaa aat cca tgt aat gca gaa ttt caa         667
Asn Arg Arg Asn Arg Lys Lys Lys Asn Pro Cys Asn Ala Glu Phe Gln
                140                   145                   150 aat ttc tgc att cac gga gaa tgc aaa tat ata gag cac ctg gaa gca         715
Asn Phe Cys Ile His Gly Glu Cys Lys Tyr Ile Glu His Leu Glu Ala
                    155                   160                   165 gta aca tgc aaa tgt cag caa gaa tat ttc ggt gaa cgg tgt ggg gaa         763
Val Thr Cys Lys Cys Gln Gln Glu Tyr Phe Gly Glu Arg Cys Gly Glu
            170                   175                   180 aag tcc atg aaa act cac agc atg att gac agt agt tta tca aaa att         811
Lys Ser Met Lys Thr His Ser Met Ile Asp Ser Ser Leu Ser Lys Ile
185                   190                   195 gca tta gca gcc ata gct gcc ttt atg tct gct gtg atc ctc aca gct         859
Ala Leu Ala Ala Ile Ala Ala Phe Met Ser Ala Val Ile Leu Thr Ala
200                   205                   210                   215 gtt gct gtt att aca gtc cag ctt aga aga caa tac gtc agg aaa tat         907
Val Ala Val Ile Thr Val Gln Leu Arg Arg Gln Tyr Val Arg Lys Tyr
                220                   225                   230 gaa gga gaa gct gag gaa cga aag aaa ctt cga caa gag aat gga aat         955
Glu Gly Glu Ala Glu Glu Arg Lys Lys Leu Arg Gln Glu Asn Gly Asn
            235                   240                   245 gta cat gct ata gca taa ctgaagataa aattacagga tatcacattg               1003
Val His Ala Ile Ala
            250 gagtcactgc caagtcatag ccataaatga tgagtcggtc ctctttccag tggatcataa       1063 gacaatggac cctttttgtt atgatggttt taaactttca attgtcactt tttatgctat       1123 ttctgtatat aaaggtgcac gaaggtaaaa agtattttt caagttgtaa ataatttatt        1183 taatatttaa tggaagtgta tttattttac agctcattaa actttttaa ccaaacagat        1243 caaaaaaaaa aaaaaaaaa aaaaaaaaa a                                        1274

<210> SEQ ID NO 2
<211> LENGTH: 252
<212> TYPE: PRT
<213> ORGANISM: Homo sapiens

<400> SEQUENCE: 2

Met Arg Ala Pro Leu Leu Pro Pro Ala Pro Val Val Leu Ser Leu Leu
1               5                   10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

Phe Glu Val Thr Ser Arg Ser Glu Met Ser Ser Gly Ser Glu Ile Ser
    50                  55                  60
```

-continued

```
Pro Val Ser Glu Met Pro Ser Ser Ser Glu Pro Ser Ser Gly Ala Asp
 65              70              75              80

Tyr Asp Tyr Ser Glu Glu Tyr Asp Asn Glu Pro Gln Ile Pro Gly Tyr
                 85              90              95

Ile Val Asp Asp Ser Val Arg Val Glu Gln Val Val Lys Pro Pro Gln
             100             105             110

Asn Lys Thr Glu Ser Glu Asn Thr Ser Asp Lys Pro Lys Arg Lys Lys
         115             120             125

Lys Gly Gly Lys Asn Gly Lys Asn Arg Arg Asn Arg Lys Lys Lys Asn
     130             135             140

Pro Cys Asn Ala Glu Phe Gln Asn Phe Cys Ile His Gly Glu Cys Lys
145             150             155             160

Tyr Ile Glu His Leu Glu Ala Val Thr Cys Lys Cys Gln Gln Glu Tyr
                165             170             175

Phe Gly Glu Arg Cys Gly Glu Lys Ser Met Lys Thr His Ser Met Ile
             180             185             190

Asp Ser Ser Leu Ser Lys Ile Ala Leu Ala Ala Ile Ala Ala Phe Met
         195             200             205

Ser Ala Val Ile Leu Thr Ala Val Ala Val Ile Thr Val Gln Leu Arg
    210             215             220

Arg Gln Tyr Val Arg Lys Tyr Glu Gly Glu Ala Glu Glu Arg Lys Lys
225             230             235             240

Leu Arg Gln Glu Asn Gly Asn Val His Ala Ile Ala
                245             250
```